US008728567B2

(12) United States Patent
Yersin et al.

(10) Patent No.: US 8,728,567 B2
(45) Date of Patent: May 20, 2014

(54) DOUBLE COMPLEX SALTS AS ABSORBERS IN OSC/OPV DEVICES

(75) Inventors: Hartmut Yersin, Sinzing (DE); Tobias Fischer, Rimbach (DE); Uwe Monkowius, Linz (AT)

(73) Assignee: Cynora GmbH, Eggenstein-Leopoldshafen (DE)

( * ) Notice: Subject to any disclaimer, the term of this patent is extended or adjusted under 35 U.S.C. 154(b) by 299 days.

(21) Appl. No.: 13/125,949

(22) PCT Filed: Oct. 22, 2009

(86) PCT No.: PCT/DE2009/001505
§ 371 (c)(1),
(2), (4) Date: May 18, 2011

(87) PCT Pub. No.: WO2010/048936
PCT Pub. Date: May 6, 2010

(65) Prior Publication Data
US 2011/0212258 A1    Sep. 1, 2011

(30) Foreign Application Priority Data

Oct. 24, 2008   (DE) .......................... 10 2008 053 107

(51) Int. Cl.
*B05D 5/12*    (2006.01)
*H01L 51/46*   (2006.01)
*H01L 51/48*   (2006.01)

(52) U.S. Cl.
USPC .............. 427/74; 427/248.1; 540/145; 546/8; 546/347; 544/255; 544/242

(58) Field of Classification Search
USPC ................. 427/74; 540/145; 546/2, 8, 9, 347; 544/255, 242
See application file for complete search history.

(56) References Cited

U.S. PATENT DOCUMENTS

| | | | |
|---|---|---|---|
| 2002/0042174 A1 | 4/2002 | Kunugi et al. | |
| 2005/0211974 A1* | 9/2005 | Thompson et al. | ............. 257/40 |
| 2010/0141120 A1 | 6/2010 | Yesin et al. | |

FOREIGN PATENT DOCUMENTS

| | | |
|---|---|---|
| CN | 1973386 A | 5/2007 |
| CN | 101087863 A | 12/2007 |
| DE | 102006030860 A1 | 1/2008 |
| EP | 0 277 032 A2 | 8/1988 |
| WO | 2005/098990 A1 | 10/2005 |
| WO | 2006/067074 A1 | 6/2006 |

OTHER PUBLICATIONS

Carrie E. Buss, et al., "Synthesis and Characterization of Pt(CN-p-(C2H5)C6H4)2(CN)2, a Crystalline Vapoluminescent Compound That Defects Vapor-Phase Aromatic Hydrocarbons", Journal of the American Chemical Society, vol. 124, Jan. 17, 2002, pp. 1031-1039, ACS.
International Preliminary Report on Patentabiity from the International Bureau and Written Opinion of the International Searching Authority, mailing date May 5, 2011 corresponding to International Application No. PCT/DE2009/001505).
US20100141120 corresponds to German Application DE102006030860.
International Search Report dated Mar. 31, 2010 corresponding to International Application No. PCT/DE2009/001505).

\* cited by examiner

*Primary Examiner* — Dah-Wei D Yuan
*Assistant Examiner* — Jose Hernandez-Diaz
(74) *Attorney, Agent, or Firm* — Ryan, Mason & Lewis, LLP

(57) ABSTRACT

The present invention pertains to the double complex salts in optoelectronic components, like organic diodes, organic transistors or organic lasers, in particular an organic solar cell (OSC, OPP) and in particular from oligomers built from charged metal complexes.

18 Claims, 5 Drawing Sheets

Schematic and simplified depiction regarding the function of an OSC

| 6 | Electrode, positive |
|---|---|
| 5 | HTL: p-conductor-Material |
| 4 | Absorption-layer |
| 3 | ETL: n-conductor-material |
| 2 | Electrode, negative |
| 1 | Carrier-material |

Assembly principle for an OSC device—general formulation.

Figure 3
| 6 | Positive electrode: Au: 60 nm |
|---|---|
| 5 | HTL: MeO-TPD: 10nm |
| 4 | Absorption-layer: 50 bis 100 nm |
| 3 | ETL: $C_{60}$: 50 nm |
| 2 | Negative electrode: ITO: 40 nm |
| 1 | Carrier material, Glass |
Example for an OSC device for the compounds of the invention. The thicknesses of the layers are merely exemplary.
Figure 4A
n-conductors:
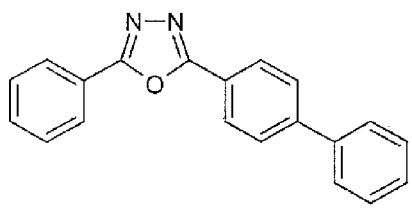
2-(4-Biphenyl)-5-phenyl-1,3,4-oxadiazol
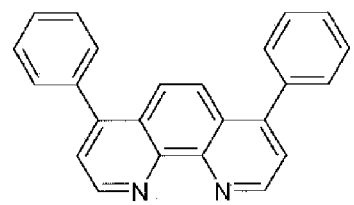
Bathocuproin
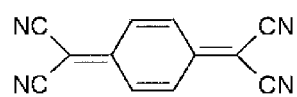
7,7,8,8-Tetracyanochinodimethan
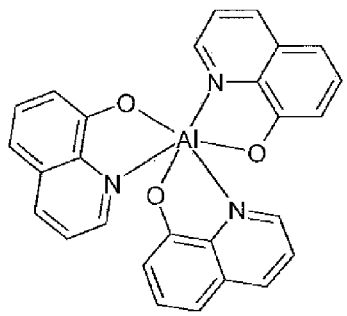
Al(III) 8-Hydroxychinolinat p-conductors:

Zink(II) Phthalocyanin

Benz[b]anthracen

Pentacen

α-Quaterthiophen 5,5'-Dihexyl-2,2'-Thiophen 1,4-Bis-(diphenylamino)benzol 1,3,5-Tris-(diphenylamino)benzol N,N,N',N'-Tetrakis-(4-Methoxyphenyl)benzidin Examples for the n and p conductor materials for OSCs.

Excitation and emission spectra of [Pt(4,4'-Dinonyl-2,2'-dipyridyl)$_2$][Pt(CN)$_4$] (T = 300 K, $\lambda_{exc.}$ = 365 nm, $\lambda_{det.}$ = 563 nm).

light

Nano-honeycomb pattern on single crystal TiO$_2$ (001) surface

DOUBLE COMPLEX SALTS AS ABSORBERS IN OSC/OPV DEVICES

CROSS-REFERENCE TO RELATED APPLICATION

This application is a National Stage application under 35 U.S.C. 371 which claims priority to International PCT Application No. PCT/EP2009/001505, filed on Oct. 22, 2009, the disclosure of which is hereby incorporated by reference herein in its entirety.

The present invention relates to double complex salts in optoelectronic components, particularly formed from oligomers of charged metal complexes for use in OSCs (OPVs).

BRIEF DESCRIPTION OF THE DRAWINGS

Exemplary embodiments of the present invention will be described below in more detail, with reference to the accompanying drawings, of which:

FIG. 3 shows an example for an OSC device in accordance with an embodiment of the present invention.

FIG. 4A shows examples of n-conductor materials for OSCs in accordance with an embodiment of the present invention.

Figures 1, 2:
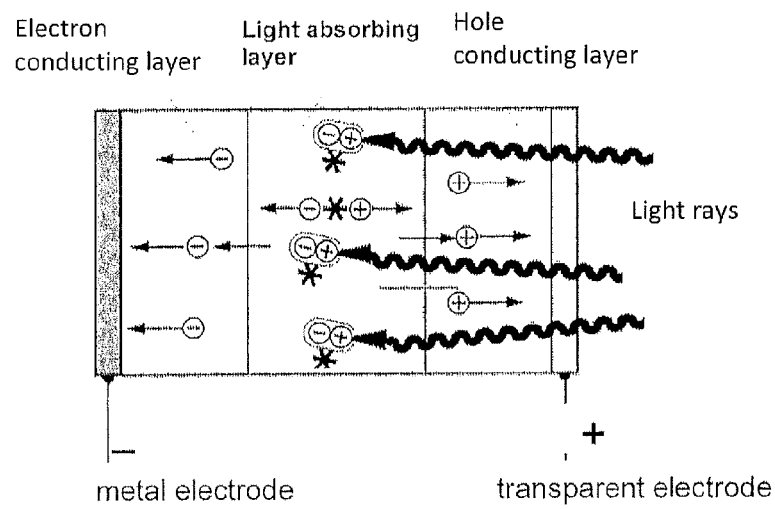
FIG. 1 shows a schematic depiction regarding the function of an Organic Solar Cell (OSC) in accordance with an embodiment of the present invention.
FIG. 2 shows an assembly principle for an OSC device in accordance with an embodiment of the present invention.

The Assembly and Functional Principle of OSCs (Organic Solar Cells)

General Note:

Often, the abbreviation OPV (=Organic photovoltaic) is used for organic solar cells (OSCs).

An important goal of this invention is the efficient conversion of the solar energy into electrical energy. The specifications associated with the structure of such a device resemble at many points the structure of OLEDs. E.g., it need to be ensured in OLEDs that holes coming from the anode and electrons coming from the cathode recombine at the dyes (organic metal emitter) and emit light. Conversely, it is important to ensure with OSCs that no further light is emitted from the dye molecules that have been excited by sunlight, but rather holes and electrons are created and travel to the cathode or to the anode, respectively. Surprisingly, the same dye materials used for OLEDs can also be used for OSCs under certain conditions, such as, when their absorption extends far enough into the red or IR spectrum.

Several technical and architectural details of the device have been suggested in order to implement OSCs. Three different types of OSCs can be distinguished:

1) OSCs in which the organic layer is composed of so-called "small molecules". (SM solar cells are produced through vacuum deposition.)
2) OSCs in which the organic layers are composed of polymers, among other materials. (Polymer solar cells are produced through spin-coating or ink-jet printing.)
3) "Dye-sensitized solar cells" with a highly porous $TiO_2$ electron conducting layer. (These are produced by sintering the $TiO_2$, and then layering it with dye.) (The principle has been put into practice in the so-called Grätzel cells).

Besides these three different types of OSCs, OSCs can also be distinguished based on their function. In general, the separation of electrical charge occurs after the absorption of photons, followed by the transport of the generated holes and electrons to their respective electrodes (see FIG. 1). Depending on the function, the separation of the charge carrier is realized through various ways. In a Grätzel cell, the dye at the surface of the electrode functions as a photo sensitizer. After the absorption of a photon, an electron transfer occurs from the excited dye to the electrode. The oxidized dye is subsequently reduced by a redox-active substance that is present in the electrolyte.

In the so-called solid solar cells (hetero junction, bulk-heterojunction and p-i-n solar cells) the charge carriers (electron and hole) are separated at a boundary layer located between different layers of the device. In doing so, the exciton (the excited state of a dye) is generated either directly at the boundary between the hole and the electron conducting layer (hetero-junction solar cell) or at an additionally established photoactive layer (p-i-n solar cell). In the latter case, the exciton is created within this photoactive layer through absorption of a photon and is transported in the direction of the hole or electron-conducting layer, where the charge separation occurs at the boundary through a heterogeneous electron-hole transfer. The photoactive layer can also be produced in a bulk-hetero-junction form, which is a mixture of hole and electron conducting material.

The most important advantages of OSCs are:
i) a relatively simple manufacturing process (there is no need, for example, of growing large, ultra-pure crystals),
ii) comparably low manufacturing temperatures,
iii) the use of organic/metallic-organic materials,
iv) the low thickness of the individual layers,
v) the low material usage (for example, only 0.1 g organic material for one square-meter of solar cell),
vi) and the possibility of producing flexible devices on plastic substances.

The assembly of an organic solar cell resembles that of an OLED, as can be deduced from FIG. 1. A cell is manufactured in a sandwich-geometry, wherein an electrode is a transparent semi-conductor that is usually made out of indium-tin oxide (ITO). One or more organic layers are applied onto this electrode: hole-conducting layer, light-absorbing layer, electron-conducting layer, and a terminal metal electrode.

In summary, the process that generates to a photon current in an organic solar cell and consists of multiple elementary steps shall be are elucidated here once more: a photon of the incoming light is absorbed by a dye-molecule in the absorption layer. As a result, the dye-molecule is electronically excited. Since the molecule in the excited state (exciton) exhibits other redox characteristics as when in the ground state, an electrical charge separation occurs within the absorption layer or at a boundary layer when the HOMO- and LUMO-positions of the hole transport layer and of the electron transport layer are chosen appropriately relative to the HOMO- and LUMO-positions of the absorption layer. The electrons and holes generated thereby travel through the respective electron transport layer or hole transport layer in the direction of the electrodes, through which an electrical tension at the electrodes is created. From this functional principle, the requirements for the substances used in the device arise:

i) a very high absorption of the dye over the entire visible spectral range up to the near IR region or a very high absorption for selected spectral ranges,
ii) relatively good hole- or electron-conductivity for the desired layers,
iii) good exciton transport in the absorption layer,
iv) effective and fast exciton dissociation, as well as fast removal of the charge carrier in the absorption layer or at one of the boundary layers in order to avoid a recombination of hole and electron.

The invention is based on the utilization of oligomers formed from double complex salts in optoelectronic components, particularly in OSCs.

The invention for use in optoelectronic components, in particular in OSCs, therefore relates to an oligomer comprising at least one, in particular at least two, positively charged metal complexes and at least one, in particular at least two, negatively charged metal complexes, whereby the metal complex comprises the

$K_1 = [L1L2L3L4M1]^{n+}$        formula (I)

$K_2 = [L5L6L7L8M2]^{n-}$        the formula (II)

wherein M1 and M2 represents, independently from each other, a metal center selected from Ir(I), Rh(I), Pt(II), Au(III) and L1, L2, and L4, as well as L5, L6, L7 and L8 represent a neutral or charged ligand, whereby two or more of the ligands L1, L2, L3 and L4 as well as L5, L6, L7 and L8 can also be bound to one another and n is either 1 or 2. The ligands L1-L8 must be chosen such that the indicated and necessary overall charge of the complex is maintained.

The invention concerns in particular the use of oligomers from oppositely charged metal complexes in optoelectrical components, preferred in OSCs, lasers, diodes or transistors. Preferably, the electronic component is chosen from OSCs, organic diode, organic transistor, or organic laser. Preferably, the optoelectronic component is not an OLED (organic light emitting device).

The oligomers comprise preferably 3, more preferably at least 4, in particular at least 5, still more preferably at least 10, and most preferred at least 20 metal complexes. Preferably, the oligomers comprise at the most 200, in particular at the most 100 metal complexes. Through the increase of the number of metal complexes in the oligomers, the absorption of the absorbing material scan often be shifted further into the red spectral range. Trimers and tetramers of the metal complexes are preferred.

The common structural feature of all complexes used in the double complex salts is that the central ion M is quadratic-planar four-fold coordinated, whereby the coordinations can be symmetrical or non-symmetrical, whereby the non-symmetrical composition is preferred.

The invention relates to the use of a class of substances that can develop an extremely intensive absorption only through a pronounced metal-metal interaction between planar, oppositely charged metal complexes. The transitions, which lead to absorption, are based, therefore, in this class of substances on metal-metal interaction of the individual complexes in the oligomer. This stands in contrast to current systems in which light absorption is based on isolated, neutral molecules.

Quadratic-planar coordinated, oppositely charged Pt(II)-complexes as well as structurally related complexes of the second and third periods of transition metals with a $d^8$-electron configuration (Pd(II), Ir(I), Rh(I) and, to a certain extend Au(III)) show a preference for the formation of metal-metal interactions and form trimers, tetramers, . . . or in general oligomers or columnar structures (the terms columnar structures, stack arrangement, oligomers and aggregates are used here as synonyms). Such compounds exhibit in the solid state intensive absorption, which result from states that emerge from the metal-metal interactions.

The invention is based on the use of oppositely charged metal complexes, that is, double complex salts, that form trimers, tetramers, etc. or in general oligomers, in optoelectronic components, which are preferably hermetically sealed from the outside. The permeability of the casing is preferably for steam $<10^{-6}$ g·m$^{-2}$·d$^{-1}$ and preferably for oxygen $<10^{-6}$ cm$^3$·m$^{-2}$·d$^{-1}$·bar$^{-1}$, respectively, are especially preferable, thereby preventing gas exchange with the surrounding environment.

The oligomers to be used according to the invention are constituted from metal complexes with the

$K_1 = [L1L2L3L4M1]^{n+}$ and        formula (I)

$K_2 = [L5L6L7L8M2]^{n-}$        the formula (II)

(n=1, 2)

The metal cores M1 and M2 of the metal complexes are chosen, independently, from Ir(I), Rh(I), Pt(II), Pd(II) or Au(III), preferably from Pt(II) and Pd(II).

According to the invention, M1 can be equal to M2, or M1 is not be equal to M2 (M1=M2 or M1≠M2). Additionally, arbitrary combinations are also possible, whereupon the charges of the individual complex components must add up to zero.

L1, L2, L3 and L4 as well as L5, L6, L7 and L8 each stand for either a neutral or a charged ligand, in particular for a monodentatate or multidentate ligand. In the following description, NL refers to neutral monodentate ligands and AL refers to anionic monodentate ligands (for a detailed description of ligands, see below). It is noted that the ligands L1, L2, L3 and L4 given in the general formula [L1L2L3L4M1]$^{n+}$ do not have to be identical to likewise ligands L1 through L4 given in another general formula [L1L2L3L4M1]$^{n+}$. The ligands themselves do not have to not possess a chromophore π-systems, since the states leading to absorption result from M-M interactions.

Preferred structures of the ligands to be used according to the invention are described in the following. Preferably, oligomers/columnar structures are used with comparatively small M-M distances in order to ensure for the high absorption in the red or near-IR spectral region important for OSCs. Also preferred are the oligomers/columnar structures with medium to large M-M distances where high absorption in the green or blue spectral region occurs, for example.

Column Structures from Singly Positively or Singly Negatively Charged Quadratic-Planar Complexes:

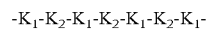

-$K_1$-$K_2$-$K_1$-$K_2$-$K_1$-$K_2$-$K_1$-

$K_1$: quadratic-planar, singly positively charged complex
$K_2$: quadratic-planar, singly negatively charged complex
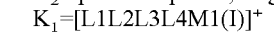
$K_1 = [L1L2L3L4M1(I)]^+$
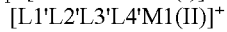
   [L1'L2'L3'L4'M1(II)]$^+$
   The ligands of the second formula are marked with an apostrophe and are therefore referred to as L1', L2', L3' or L4'. These ligands can/must be different ligands then those without the apostrophe in order to achieve charge equalization.

K₂=[L5L6 L7L8M2(I)]⁻
[L5'L6'L7'L8'M2(II)]⁻
with M1(I)/M2(I)=Ir(I), Rh(I)
M1(II)/M2(II)=Pt(II), Pd(II)

The structures of the complexes and the ligands L1, L2, L3, L4, L5, L6, L7 and L8 as well as L1', L2', L3', L4', L5', L6', L7' and L8' are elucidated with the help of the following general formulas and examples.

Examples of Double Complex Salts with $K_1$=[L1L2L3L4Pt(II)]⁺

$K_2$=[L5L6L7L8Pt(II)]⁻

Examples of the Component $K_1$=[L1L2L3L4Pt(II)]⁺:

General formula of α-diimine complexes

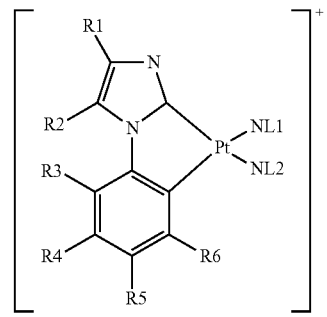

General formula of cyclometal-forming carbene-Pt complexes

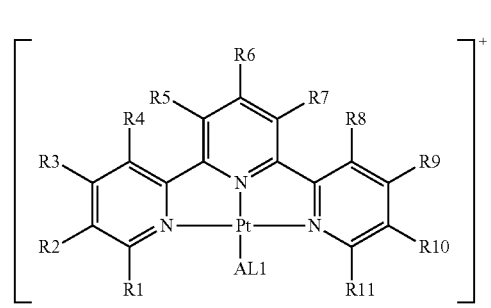

wherein, the diimine- and carbene-ligands, and the moiety R1 to R20, NL1 to NL4 as well as AL1 to AL4 are defined in "Definition of Ligands and Moieties" herein.

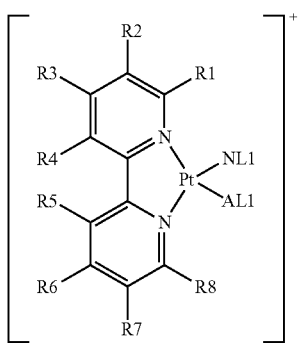

3

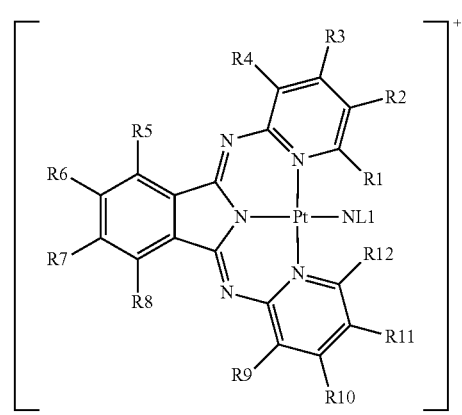

4

5

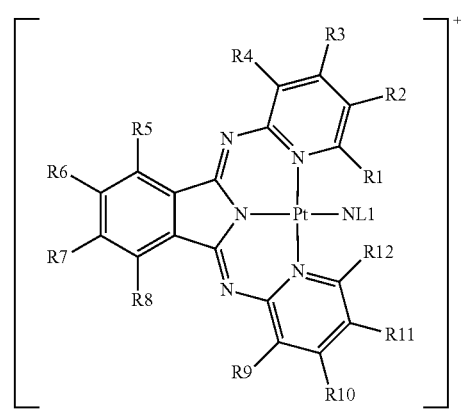

6

7

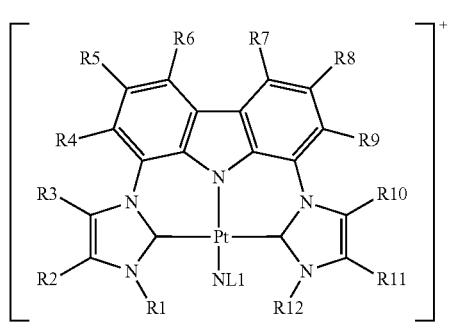 8
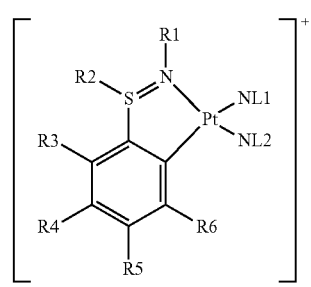 13
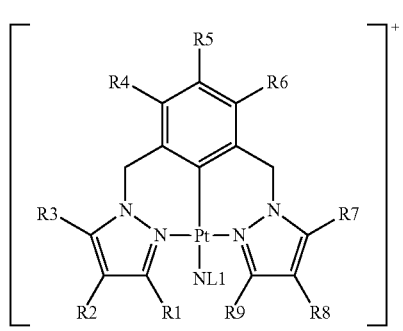 9
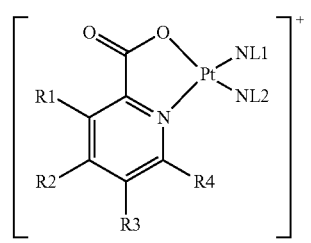 14
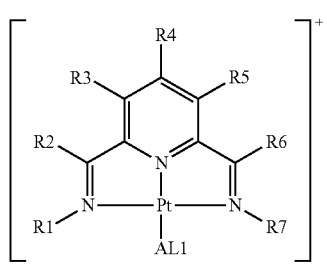 10
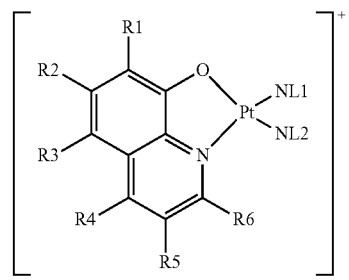 15
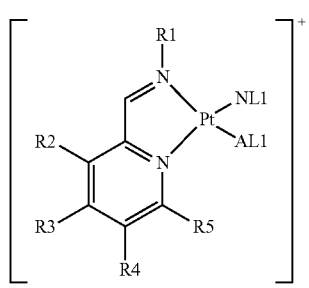 11
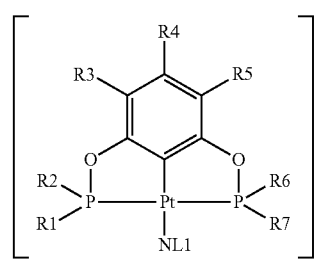 16
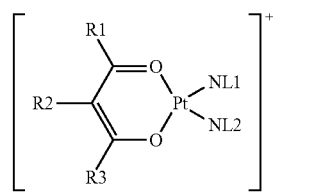 17
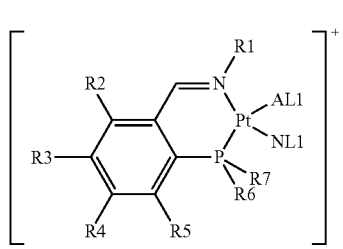 12
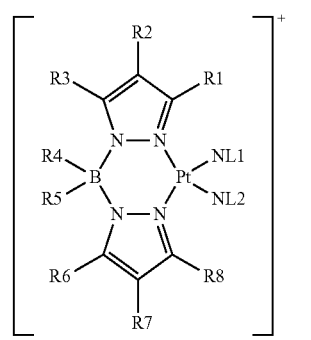 18

-continued
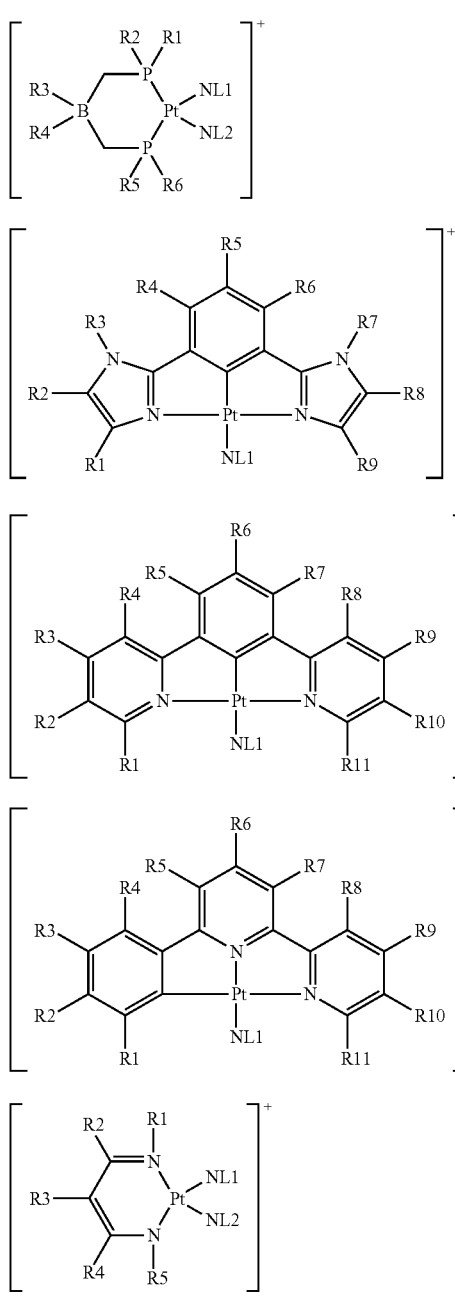
Examples of the Component $K_2=[L5L6L7L8Pt(II)]^-$:
general formula:
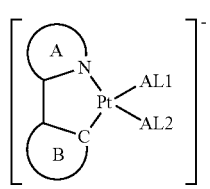
This formula is defined more precisely below (see section: Definition of Ligands and Moieties).
Example:
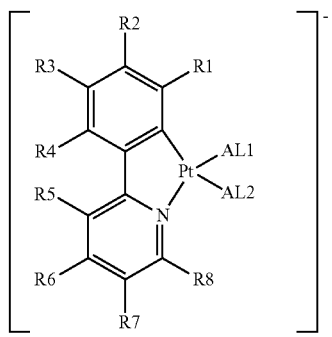
Further examples:
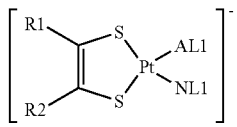
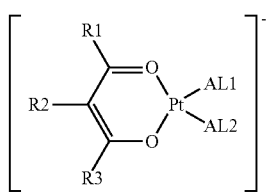
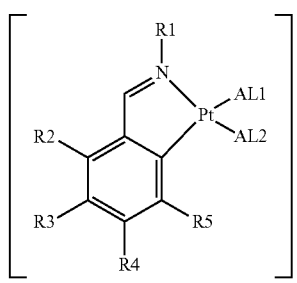
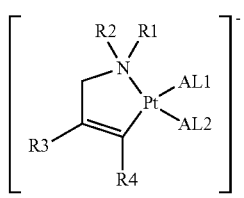

Examples of the Component $K_1=[L1L2L3L4Pd(II)]^+$:

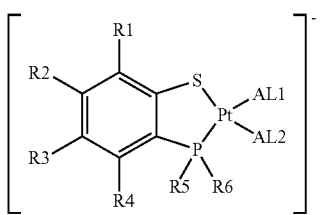

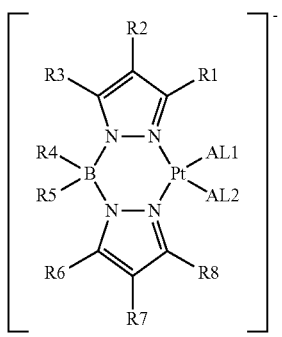

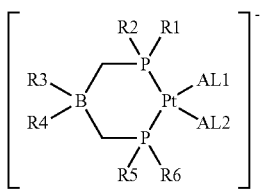

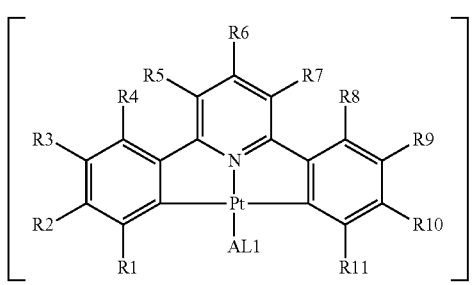

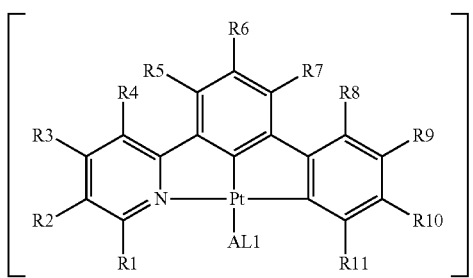

Examples of Double Complex Salts with $K_1=[L1L2L3L4Pd(II)]^+$ $K_2=[L5L6L7L8Pd(II)]^-$

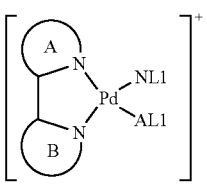

General formula of α-diimine complexes

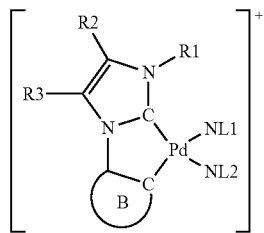

General formula of cyclometal-forming carbene-Pd complexes wherein the diimine- and carbene-ligands, and the moieties R1 to R20, NL1 to NL4 as well as AL1 to ALA are defined herein (see section: Definition of Ligands and Moieties).

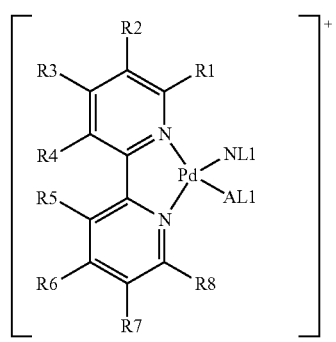

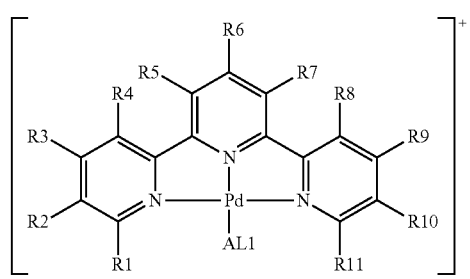

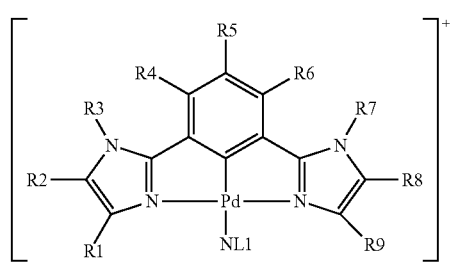

Examples of the Component $K_2=[L5L6L7L8Pd(II)]^-$:
general formula:

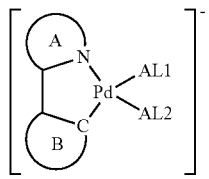

This formula is defined more precisely below (see section: Definition of Ligands and Moieties).

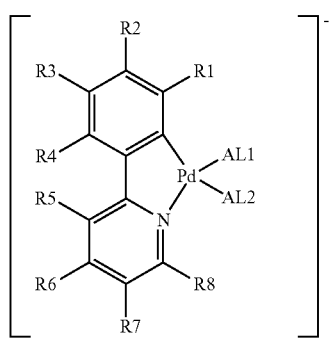

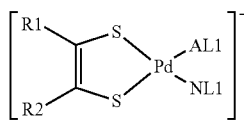

In addition to the examples cited here for $K_1=[L1L2L3L4Pd(II)]^+$ und $K_2=[L5L6L7L8Pd(II)]^-$, all the singly positively or negatively charged Pt-complexes shown above can be used when Pt is replaced by Pd.

Examples of Double Complex Salts with $K_1=[L1L2L3L4Ir(I)]^+$
$K_2=[L5L6L7L8Ir(I)]^-$ Examples of the Component $K_1=[L1L2L3L4Ir(I)]^+$:
General Formulas:

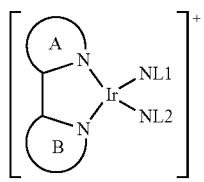

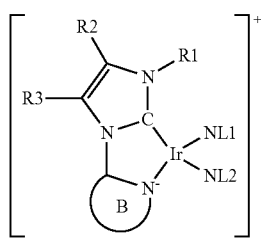

wherein the diimine- and carbene-ligands, the moieties R1 to R20, NL1 to NlA as well as AL1 to AL4 are as defined herein (see section: Definition of ligands and Moieties).

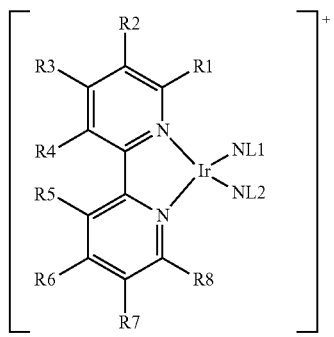

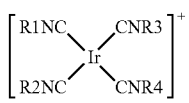

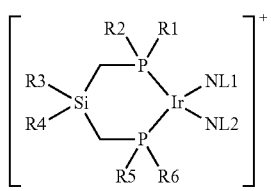

Examples of the Component $K_2=[L5L6L7L8Ir(I)]^-$:

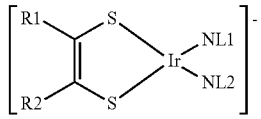

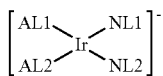

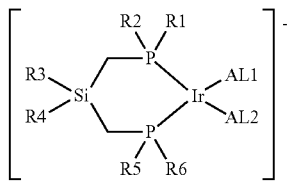

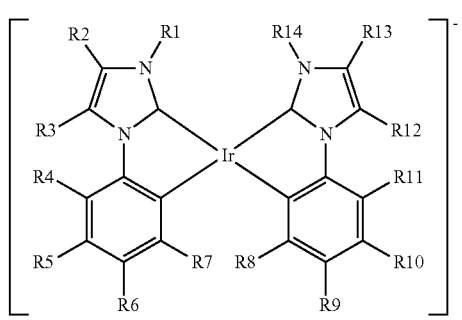

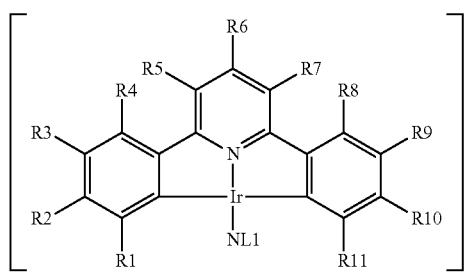
53
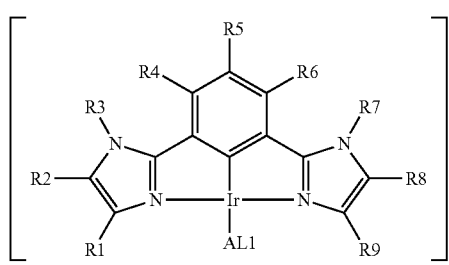
54
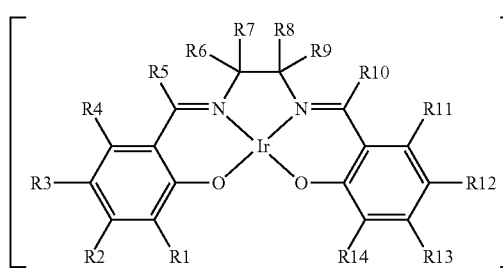
55
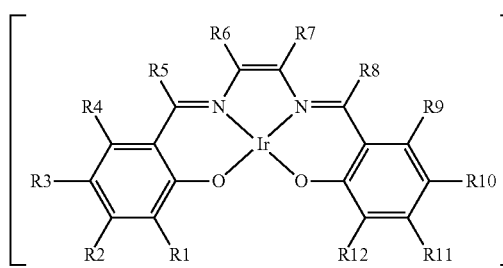
56
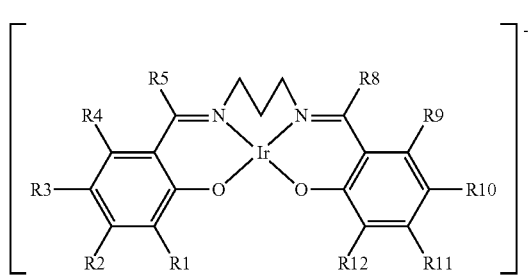
57
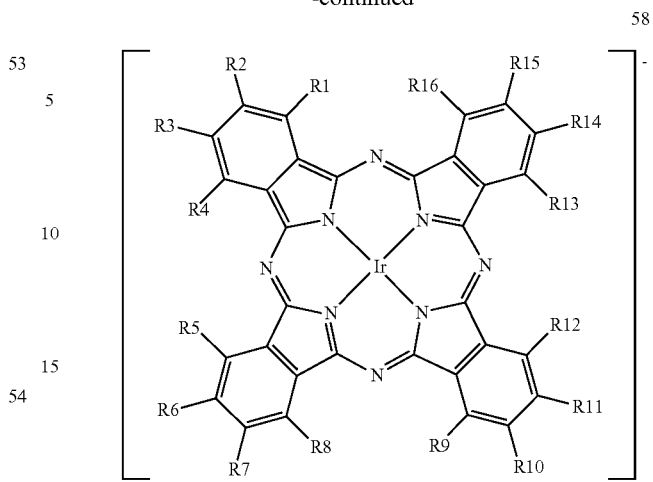
58
Examples of Double Complex Salts with $K_1=[L1L2L3L4Rh(I)]^+$
$K_2=[L5L6L7L8Rh(I)]^-$
Examples of the Component $K_1=[L1L2L3L4Rh(I)]^+$:
General Formulas:
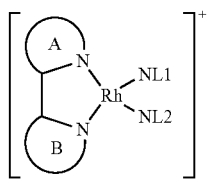
59
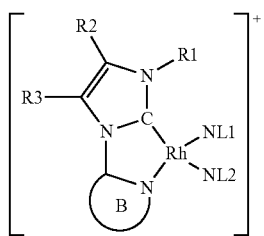
60
wherein the diimine- and carbene-ligands, and the moieties R1 to R20, NL1 to NL4 as well as AL1 to AL4 are defined herein (see section: Definition of Ligands and Moieties).
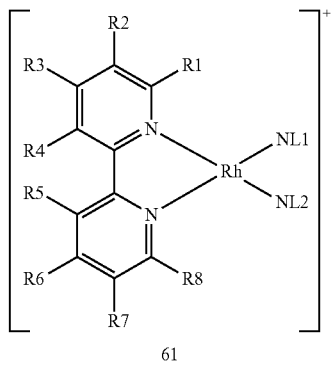
61

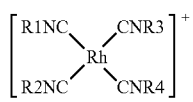

Examples of the Component $K_2 = [L5L6L7L8Rh(I)]^-$:

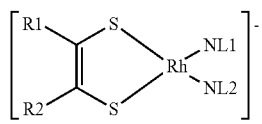

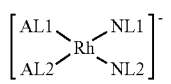

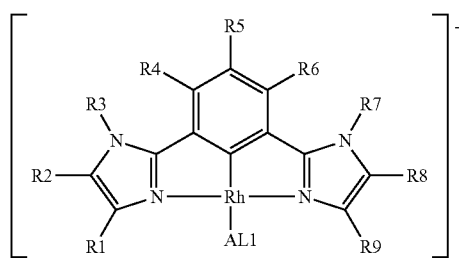

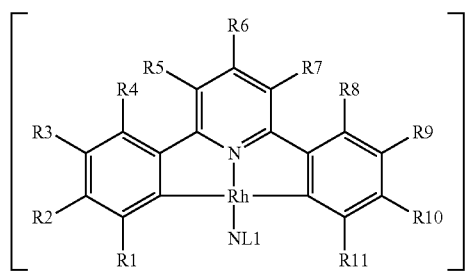

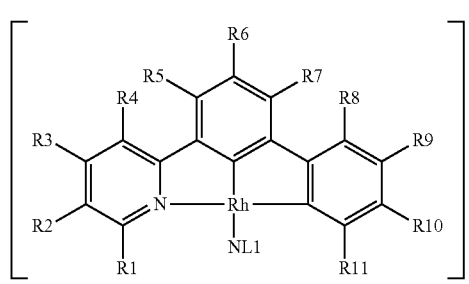

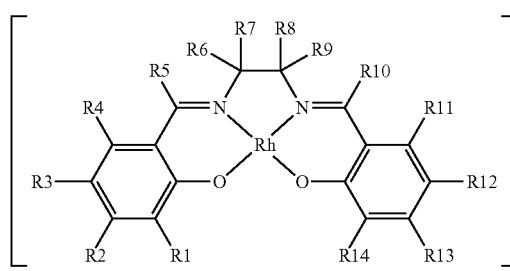

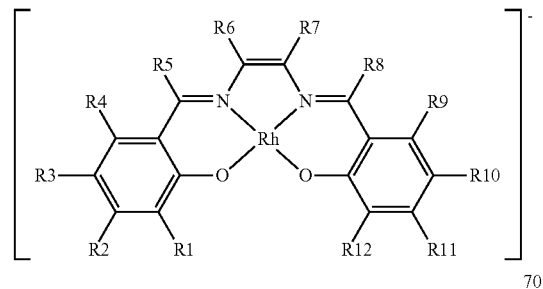

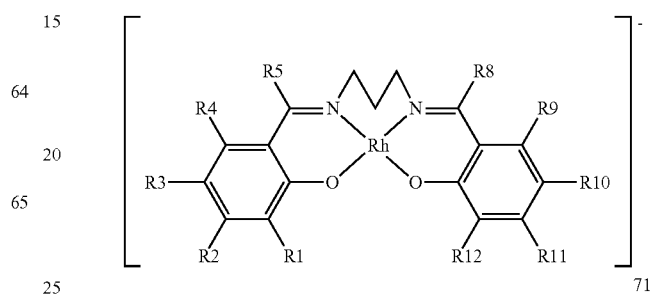

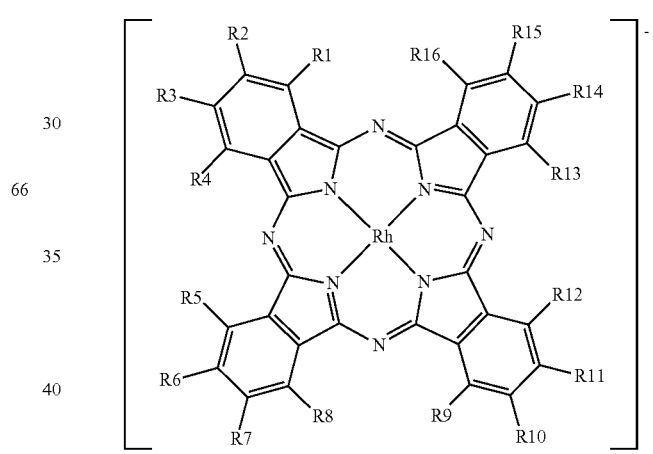

Column Structures that are Built from Doubly Positively or Doubly Negatively Charged Quadratic-Planar Complexes:

$$-K_1-K_2-K_1-K_2-K_1-K_2-K_1-$$

$K_1$: quadratic-planar, doubly positively charged complex
$K_2$: quadratic-planar, doubly negatively charged complex
$K_1 = [L1L2L3L4M1(II)]^{2+}$
$K_2 = [L5L6L7L8M2(II)]^{2-}$ with M1(II), M2(II)=Pt(II), Pd(II)

Examples of Double Complex Salts with $K_1 = [L1L2L3L4Pt(II)]^{2+}$
$K_2 = [L5L6L7L8Pt(II)]^{2-}$ Examples of Components $K_1 = [L1L2L3L4Pt(II)]^{2+}$:

As cationic complexes, α-diimine complexes such as 74-78, carbene complexes such as 83-84, Pinzer complexes such as 85-103 as well as generally quadratic-planar platinum complexes (104) with neutral ligands NL1-NL4 can be used.

General formulas (rings C and D are defined analogously to A and B (see below))

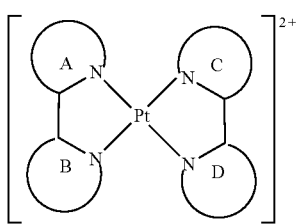
72
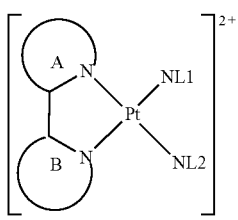
73
wherein the diimine- and carbene-ligands, the moieties R1 to R20, NL1 to NL4 as well as AL1 to AL4 are as defined herein (see section: Definition of Ligands and Moieties).
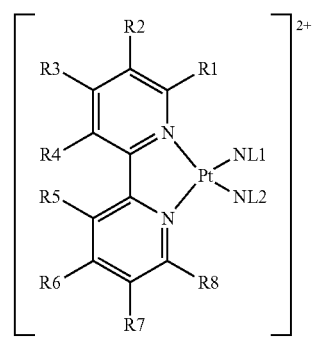
77
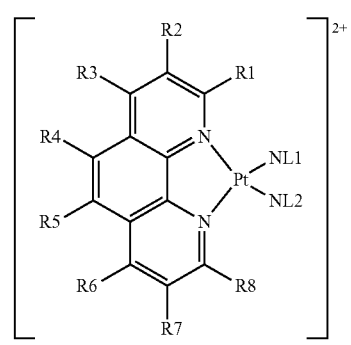
78
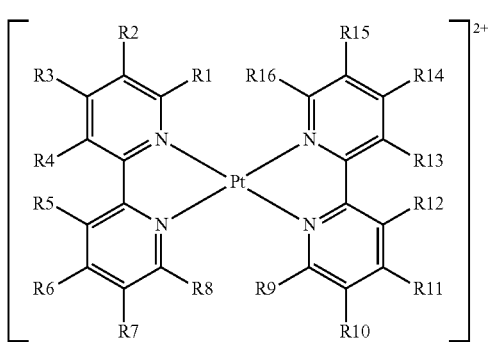
74
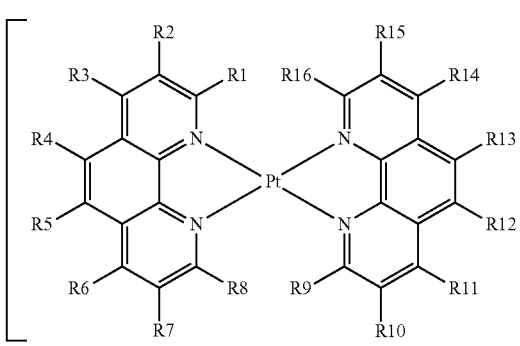
75
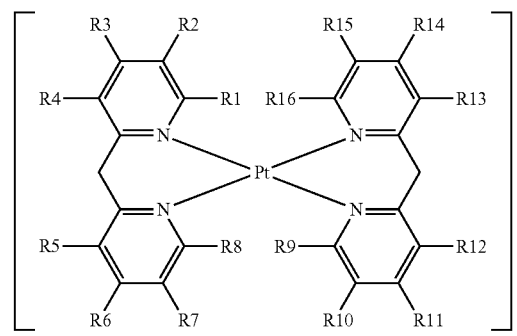
79
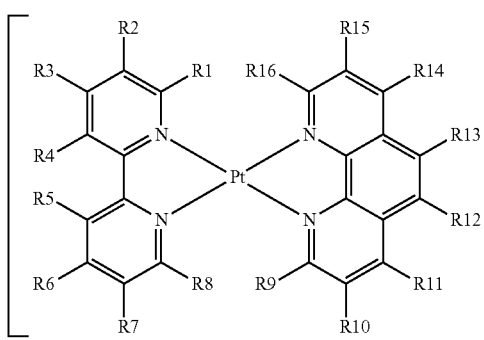
76
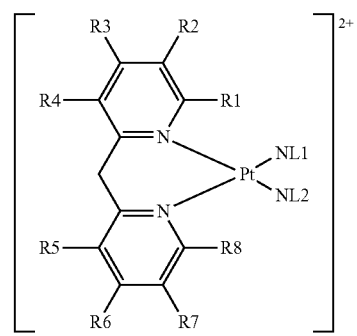
80

General formulas:
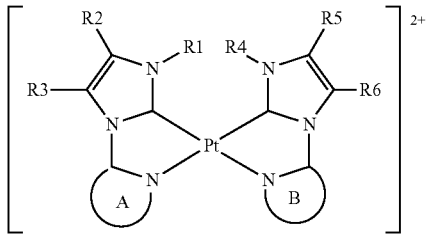
81
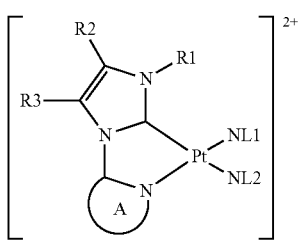
82
wherein the carbene-ligands, and the moieties R1 to R20, NL1 to NL4 as well as AL1 to AL4 are defined herein (see sections: Definition of Ligands and Moieties).
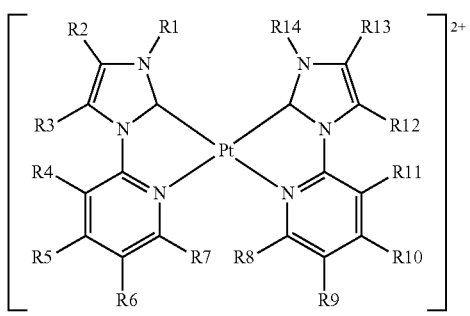
83
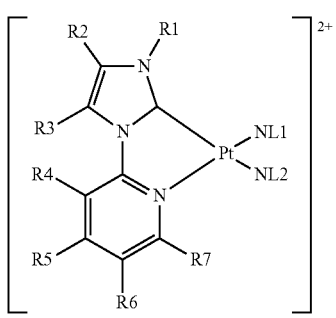
84
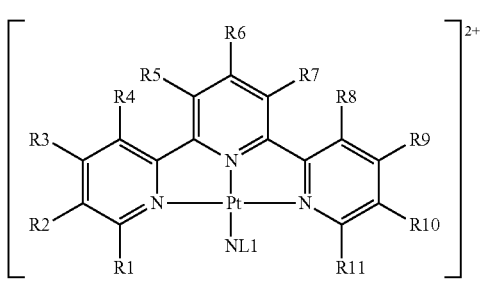
85
-continued
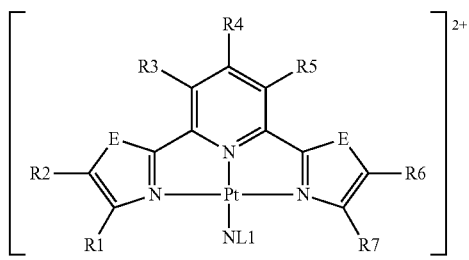
86
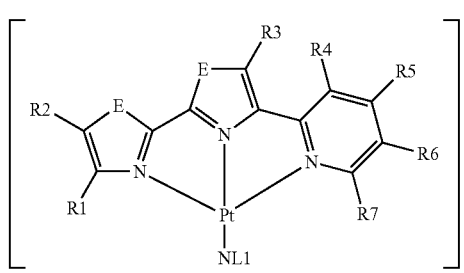
87
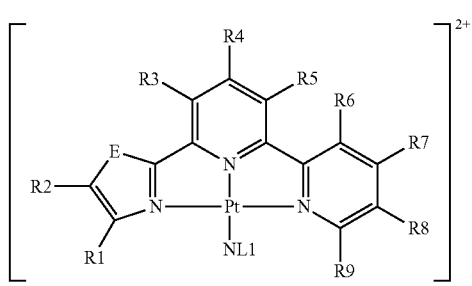
88
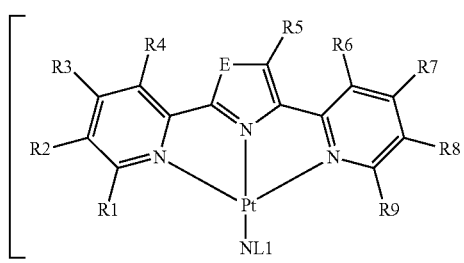
89
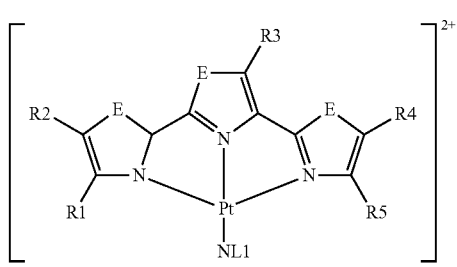
90

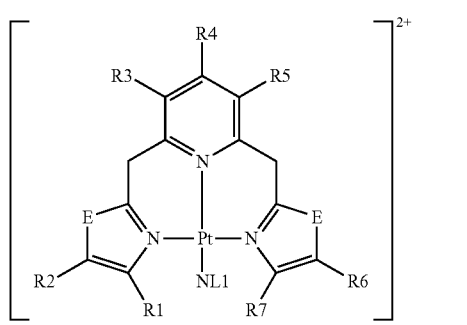 91
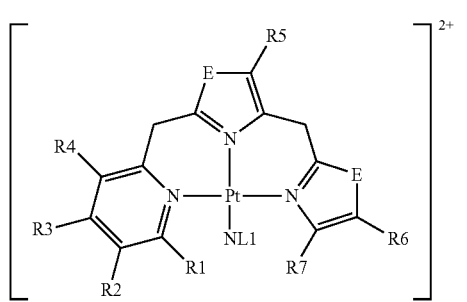 92
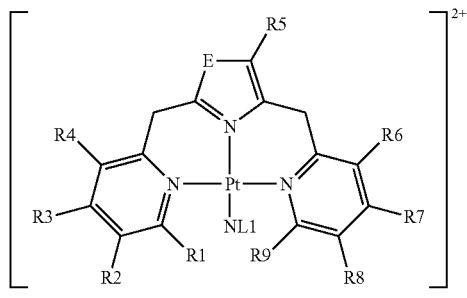 93
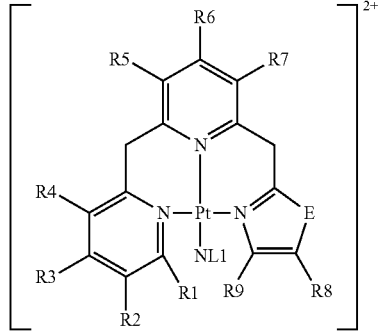 94
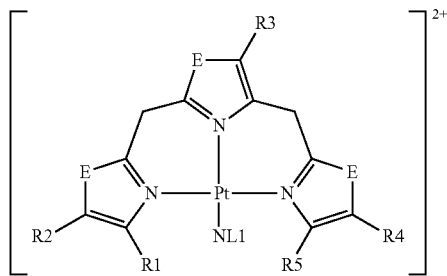 95
 96
 97
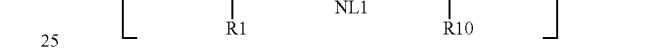 98
 99
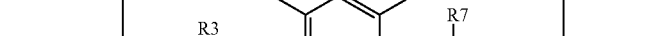 100

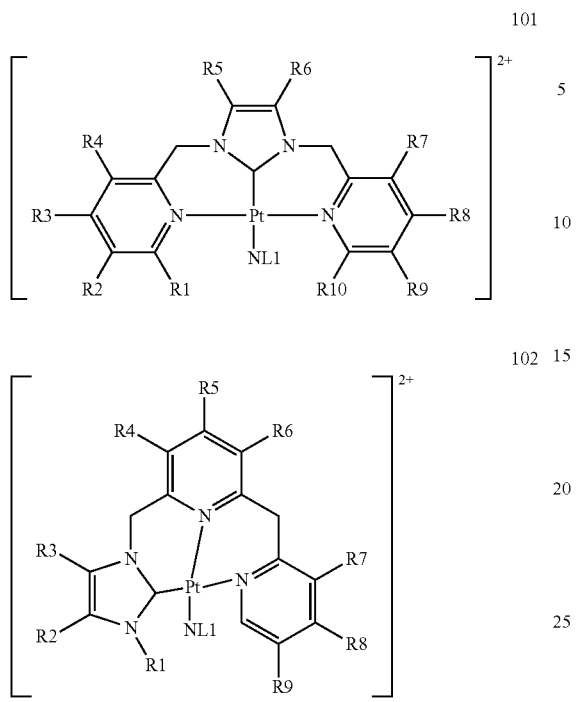
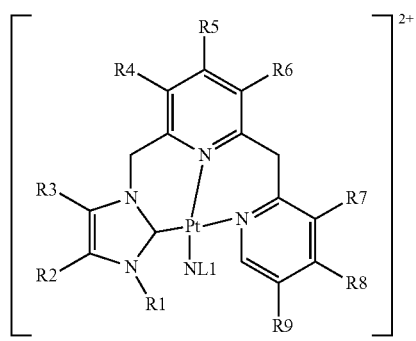
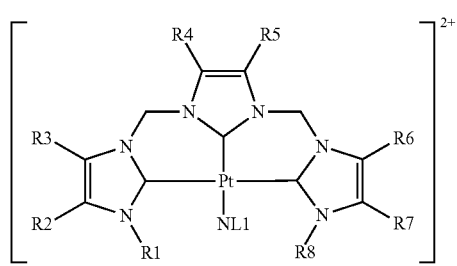
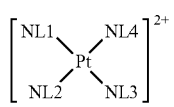
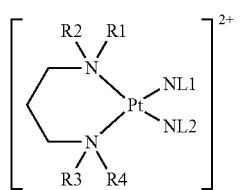
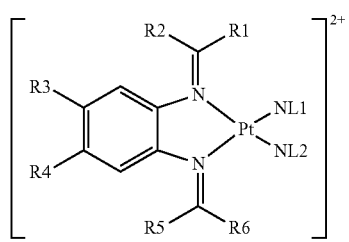
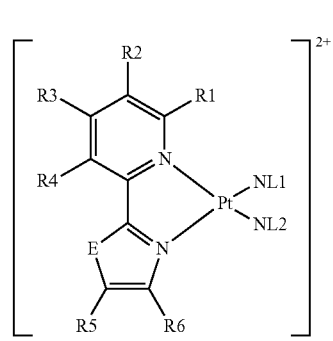
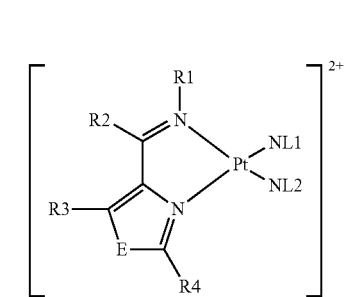
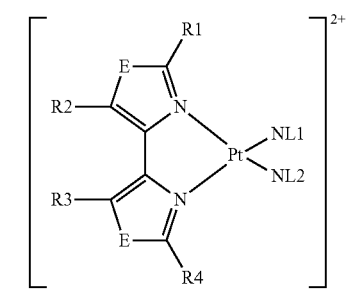
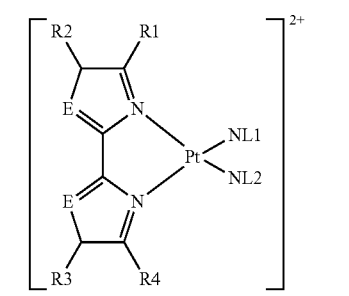
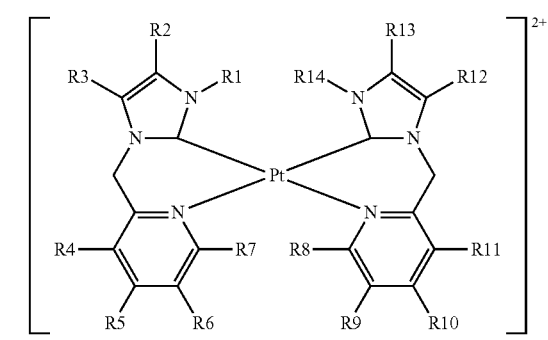

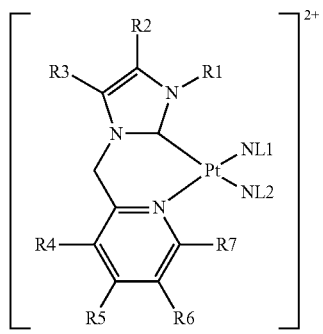
112
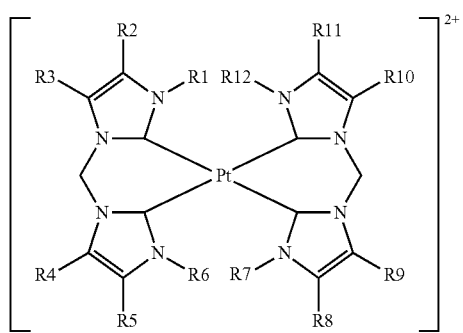
113
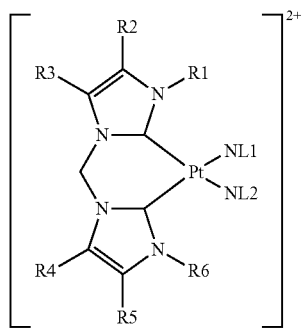
114
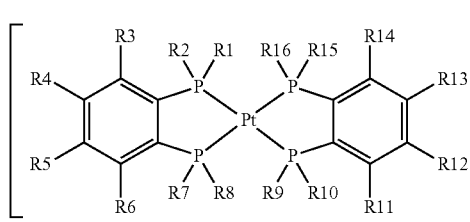
115
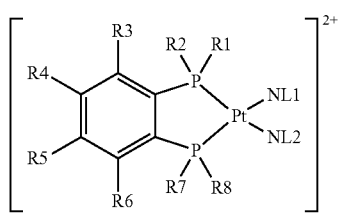
116
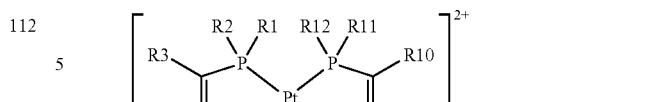
117
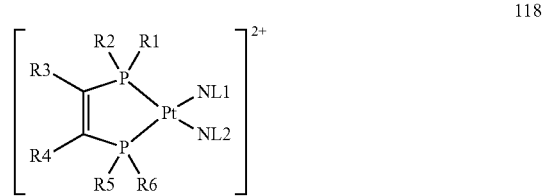
118
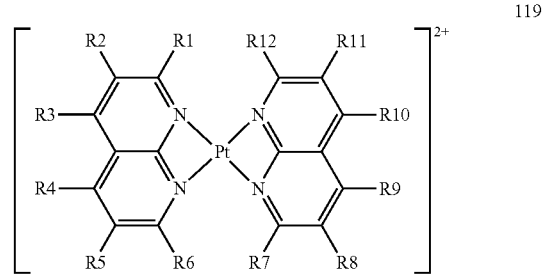
119
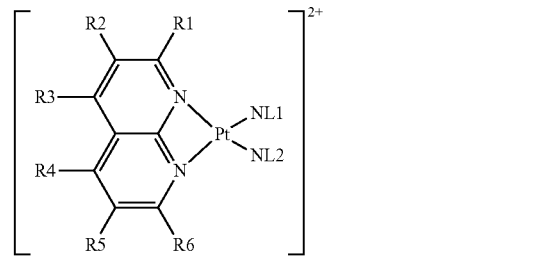
120
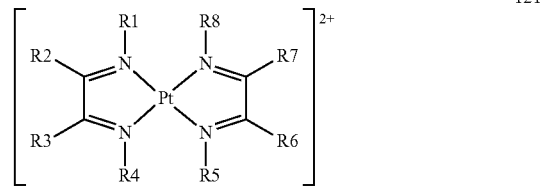
121
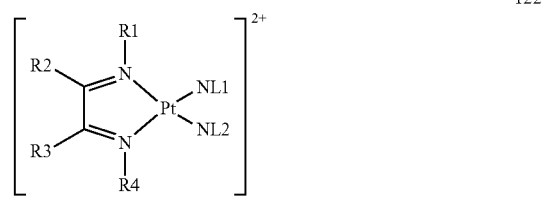
122
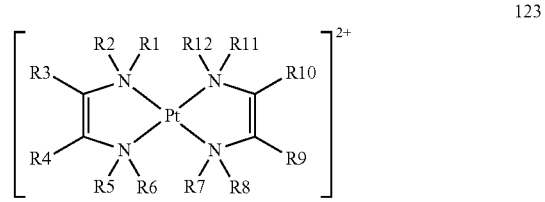
123

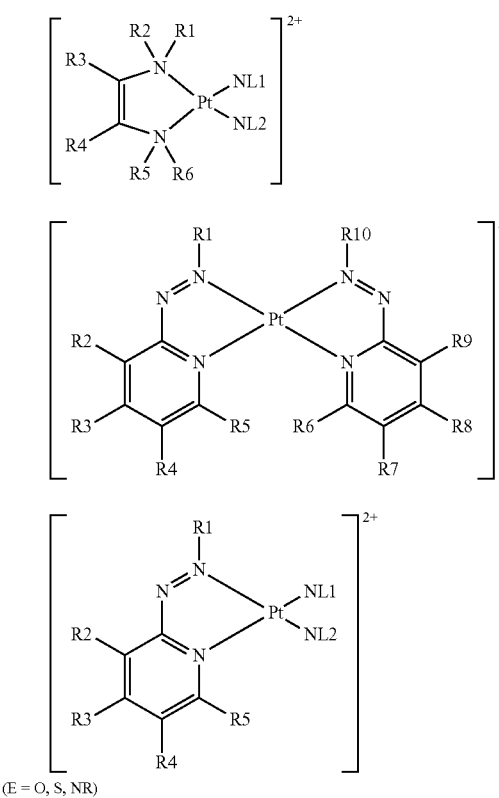

(E = O, S, NR)

Examples of the Component $K_2$=[L5L6L7L8Pt(II)]$^{2-}$:

[Pt(CN)$_4$]$^{2-}$ (127) can be preferably used as a complex anion. But also other anion complexes such as, for example, [PtCl$_4$]$^{2-}$ (128), [PtBr$_4$]$^{2-}$ (129), [PtI$_4$]$^{2-}$ (130), [Pt(C≡CR)$_4$]$^{2-}$ (131), [Pt(ox)$_2$]$^{2-}$ (132), [Pt(1,2-dithiolat-ligand)$_2$]$^{2-}$ (133) or [Pt(1,1-dithiolat-ligand)$_2$]$^{2-}$ (134), which permit M-M-interactions, can be employed.

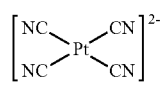

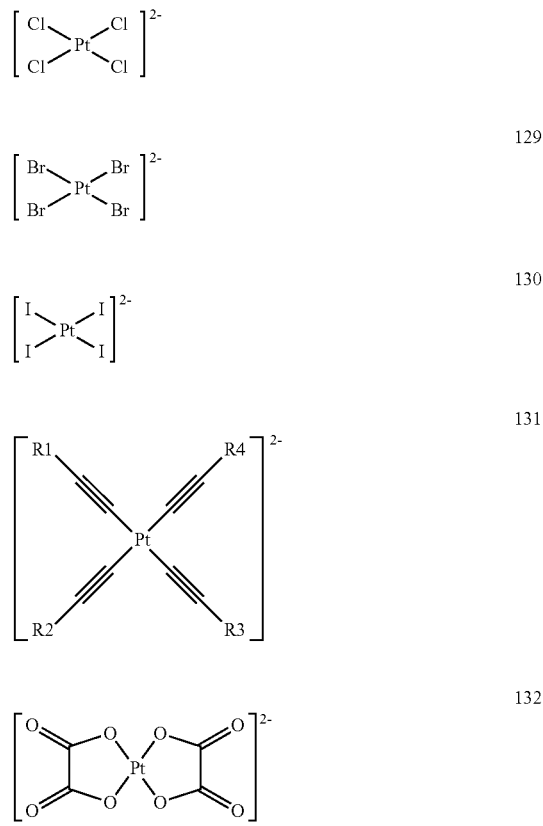

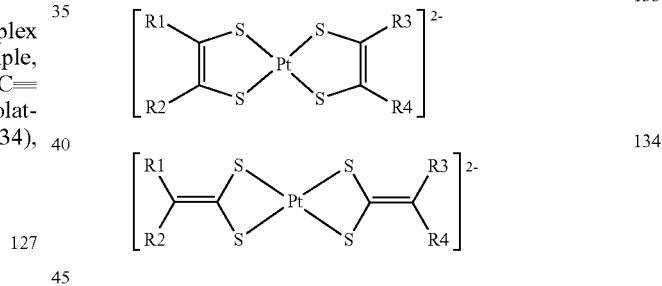

Structures 135-141 depicts complex anions according to the general structures given in the examples 133 and 134:

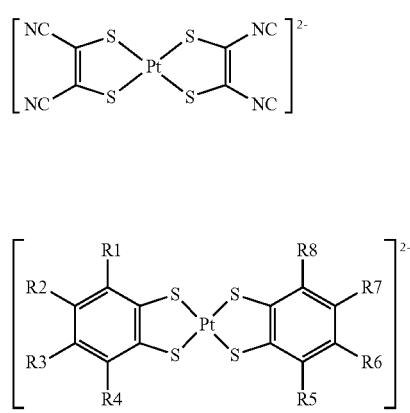

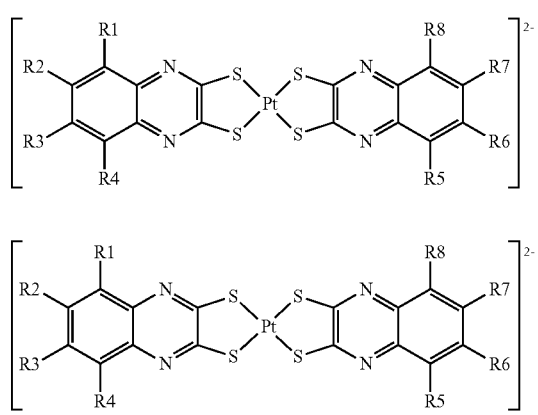

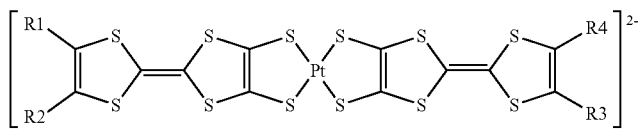

139

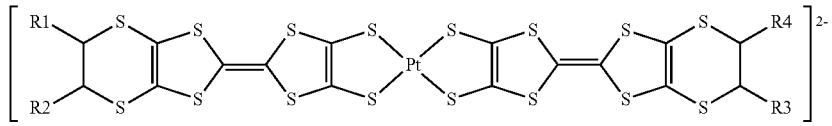

140

141

142

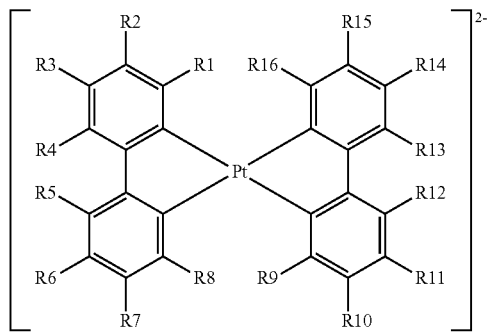

143

144

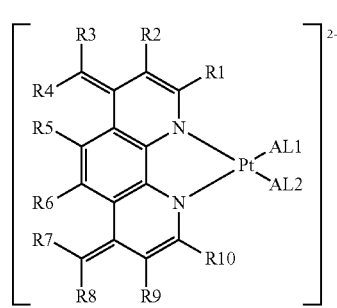

145

146

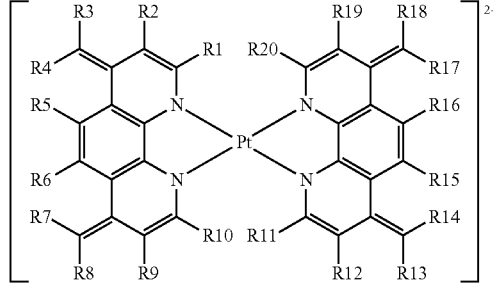

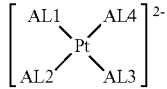

147

Examples of Double Complex Salts with $K_1=[L1L2L3L4Pd(II)]^{2+}$
$K_2=[L5L6L7L8Pd(II)]^{2-}$ Examples of the Component $K_1=[L1L2L3L4Pd(II)]^{2+}$:

As examples of doubly positively charged quadratic-planar Pd(II) complexes, the above specified examples for $K_1=[L1L2L3L4Pt(II)]^{2+}$ can also be used; however Pt(II) must be replaced by Pd(II).

Examples of Component $K_2=[L5L6L7L8Pd(II)]^{2-}$:

As examples of double negatively charged quadratic-planar Pd(II) complexes, the above specified examples for für $K_2=[L5L6L7L8Pt(II)]^2$ can also be used; however Pt(II) must be replaced by Pd(II).

Double Complex Salts Composed of Oppositely Charged Complexes with Different Central Metals
Doped Columnar Structures

-$K_1$-$K_2$-$K_1$-$K_2$-$D_1$-$K_2$-$K_1$-$K_2$-$K_1$- or

-$K_2$-$K_1$-$K_2$-$K_1$-$D_2$-$K_1$-$K_2$-$K_1$-$K_2$-

Also preferred is a doping with charged, quadratic-planar Pt-complexes (D) that are introduced in low concentrations into a chain of charged, quadratic-planar Pd-complexes (K1, K2). Thereby, the range of absorption of the Pt-compound can be shifted. In this process, the Pd-complex stack functions like a matrix interacting with the doped Pt-complex. As a result of this principle, a shift of the absorption maxima and a change of the emissions occur. The doping can be performed on columnar structures that are made up of singly or doubly charged complexes (K1, K2).

Doped columnar structures can preferably be used in optoelectronic components like lasers, diodes, or transistors.

Most preferred, doped columnar structures can be used to elicit a blue emission. A shift or influence on the wavelength of the emission towards the blue wavelength is often desired in laser applications.

Examples:
a) quadratic-planar, singly positively charged Pd-complex
  $K_2$: quadratic-planar, singly negatively charged Pd-complex
  $D_1$: quadratic-planar, singly positively charged Pt-complex
  $D_2$: quadratic-planar singly negatively charged Pt-complex
b) $K_1$: quadratic-planar, doubly positively charged Pd-complex
  $K_2$: quadratic-planar, doubly negatively charged Pd-complex
  $D_1$: quadratic-planar, doubly positively charged Pt-complex
  $D_2$: quadratic-planar, doubly negatively charged Pt-complex It is further possible to introduce singly or doubly charged Pd-complexes into columnar structures that are made up from singly or doubly charged Pt-complexes. Thereby, the sizes of the oligomers responsible for light absorption can be varied and thus, the absorption wavelength can be varied.

According to the invention, the concept of doping can also be applied to columnar structures that are made up from charged complexes of the elements Ir(I) and Rh(I). Every quadratic-planar complex with the suitable charge can be doped into the respective columnar structure.

The complex used for doping is present in the oligomer matrix preferably in a molar ratio of at the most 1:3, preferably at the most 1:10, preferably at the most 1:50 and particularly preferred at the most 1:100, based on the complexes that form the oligomer matrix. Preferably, the complex used for doping is present in the oligomer matrix in a molar ratio of at least 1:100,000, preferably at least 1:10,000, more preferred at least 1:1,000, based on the complexes forming the oligomer matrix.

The described concept of doping columnar structures can preferably be used for influencing the absorption and emission wavelengths and is therefore of great importance for OSC application. This concept of the invention is characterized in particular through the fact that, due to defined charges of the doped complexes, D1 or D2, no -D1-D1- or -D2-D2- neighbors can be present according to the principle of the invention.

Columnar Structures that are Made of Singly Positive/Negative or Doubly Positive/Negative Charged Quadratic-Planar Complexes with Different Metal Centers:

In addition to the double complex salts described above, double complex salts with different metal centers in stoichiometric compositions (non-doped) can occur. In a further preferred form, a further component is doped.

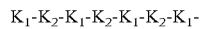

Such structures can be used for all optoelectronic components mentioned herein, preferably for OSCs.

Examples
$K_1$: quadratic-planar, singly positively (negatively) charged complex
$K_2$: quadratic-planar, singly negatively (positively) charged complex
$K_1 = [L1L2L3L4M1(I)]^+$
  $[L1'L2'L3'L4'M1(II)]^+$
$K_2 = [L5L6L7L8M2(I)]^-$
  $[L5'L6'L7'L8'M2(II)]^-$
with M1(I)/M2(I)=Ir(I), Rh(I)
  M1(II)/M2(II)=Pt(II), Pd(II)

Therefrom, the following columnar structures can, for example, be deduced:
$K_1 = [L1L2L3L4Pt(II)]^+$
$K_2 = [L5L6L7L8Pd(II)]^-$
$K_1 = [L1L2L3L4Pd(II)]^+$
$K_2 = [L5L6L7L8Pd(II)]^-$
$K_1 = [L1L2L3L4Pt(II)]^+$
$K_2 = [L5L6L7L8Ir(I)]^-$
$K_1 = [L1L2L3L4Ir(I)]^+$
$K_2 = [L5L6L7L8Pt(II)]^-$
$K_1 = [L1L2L3L4Pt(II)]^+$
$K_2 = [L5L6L7L8Rh(I)]^-$
$K_1 = [L1L2L3L4Rh(I)]^+$
$K_2 = [L5L6L7L8Pt(II)]^-$
$K_1 = [L1L2L3L4Pd(II)]^+$
$K_2 = [L5L6L7L8Ir(I)]^-$
$K_1 = [L1L2L3L4Ir(I)]^+$
$K_2 = [L5L6L7L8Pd(II)]^-$
$K_1 = [L1L2L3L4Pd(I)]^+$
$K_2 = [L5L6L7L8Rh(I)]^-$
$K_1 = [L1L2L3L4Rh(I)]^+$
$K_2 = [L5L6L7L8Pd(II)]^-$
$K_1 = [L1L2L3L4Ir(I)]^+$
$K_2 = [L5L6L7L8Rh(I)]^-$
$K_1 = [L1L2L3L4Rh(I)]^+$
$K_2 = [L5L6L7L8Ir(I)]^-$ $K_1$: quadratic-planar, doubly positively (negatively) charged complex
$K_2$: quadratic-planar, doubly negatively (positively) charged complex
$K_1 = [L1L2L3L4M1(II)]^{2+}$
$K_2 = [L5L6L7L8M2(I)]^{2-}$
  $[L5'L6'L7'L8'M2(II)]^{2-}$
with M2(I)=Ir(I), Rh(I)
  M1(II)/M2(II)=Pt(II), Pd(II)

Therefrom, the following double complex salt columnar structures follow:
$K_1 = [L1L2L3L4Pt(II)]^{2+}$
$K_2 = [L5L6L7L8Pd(II)]^{2-}$
$K_1 = [L1L2L3L4Pd(II)]^{2+}$
$K_2 = [L5L6L7L8Pt(II)]^{2-}$
$K_1 = [L1L2L3L4Pt(II)]^{2+}$
$K_2 = [L5L6L7L8Ir(I)]^{2-}$
$K_1 = [L1L2L3L4Pt(II)]^{2+}$
$K_2 = [L5L6L7L8Rh(I)]^{2-}$
$K_1 = [L1L2L3L4Pd(II)]^{2+}$
$K_2 = [L5L6L7L8Ir(I)]^{2-}$
$K_1 = [L1L2L3L4Pd(I)]^{2+}$
$K_2 = [L5L6L7L8Rh(I)]^{2-}$ The ligands denoted L1 to L8 and to L8' in a metal complex combination are not necessarily identical with those of another combination with ligands L1 to L8 as well as L1' to L8'.

Further Combinations:

The following kinds of columnar structures are also possible (examples):

Complex Salt Oligomer Made Up from Three or More Different Complexes

Examples for a Triple Combination

-K$_1$-K$_2$-K$_3$-K$_1$-K$_2$-K$_3$-K$_1$-

K$_1$=[L1L2L3L4M1(II)]$^{2+}$
K$_2$=[L5L6L7L8M2(II)]$^{-}$
K$_3$=[L5L6L7L8M2(II)]$^{-}$
K$_1$=[L5L6L7L8M2(II)]$^{2-}$
K$_2$=[L1L2L3L4M1(II)]$^{+}$
K$_3$=[L1L2L3L4M1(II)]$^{+}$
K$_1$=[L1L2L3L4M1(II)]$^{2+}$
K$_2$=[L5L6L7L8M2(I)]$^{-}$
K$_3$=[L5L6L7L8M2(I)]$^{-}$
K$_1$=[L5L6L7L8M2(II)]$^{2-}$
K$_2$=[L1L2L3L4M1(I)]$^{+}$
K$_3$=[L1L2L3L4M1(I)]$^{+}$

L1 to L4 and L5 to L6 each stand independently for a neutral or charged ligand, in particular for a monodentate or multidentate ligand. The ligands L1 to L8 need to be chosen such that the necessary overall charge of the complex is maintained.

The ligands denoted L1 to L8 as well as L1' to L8' in a metal complex combination are not necessarily identical with another combination of ligands denoted L1 to L8 as well as L1' to L8'.

Definition of the Ligands and Moieties

In so far as used herein, the ligands NL1 to NL4 are neutral ligands, e.g. carbonyl CO, nitrile NCR', isonitrile CNR" (R' and R" are defined as R1 to R20) or oxazole. For example, nitrile or isonitrile can be used that are substituted with a large organic functional group (organic group, moiety) R' or R" (R' and R" are defined as R1 to R20). As neutral ligands, compounds are also possible that coordinate via N, P, S, O, As or Se.

In so far as used herein, the ligands AL1 to AL4 are anionic ligands, e.g. cyanide CN, chloride Cl$^{-}$, bromide Br$^{-}$, iodide I$^{-}$, RS$^{-}$, RO$^{-}$, SCN$^{-}$, OCN$^{-}$, aryl groups, alkenyl, alkinyl groups or borate.

α-diimine ligands, as used herein, can consist of five or six rings, whose components Z1 to Z12 are either the fragments CR(X) (R(X)=see definition of R1-R20) or N, E can be either NR, O or S. This definition also allows for the possibility that the units A and B do not form a ring, but form an open chain. ("#" denotes the atom that is bound to the second unit):

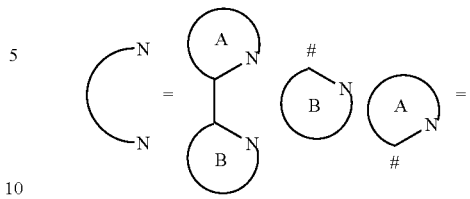

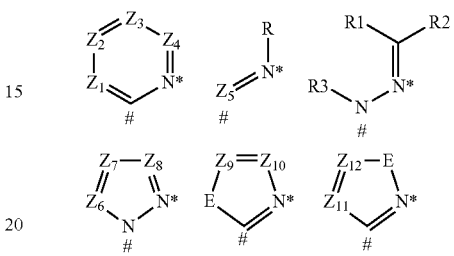

In so far as used herein, the term carbon ligand refers in particular to:

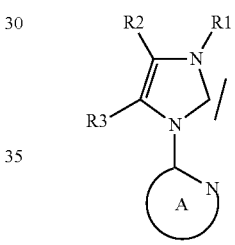

Cyclometal forming ligands as far as used herein, are bidentate, singly negatively charged ligands, which 1) bind on the one hand via sp$^2$-carbon and on the other hand via a nitrogen atom. The units A and B can consist of five or six rings and can also be open chains. The components Z1 to Z26 consisting of either the fragment CR(X) (R(X)=organic moiety defined as R1-R20) or N, E can be either NR, O or S. ("*" denotes the atom forming the complex bond, "#" denotes the atom that is bound to the second unit):

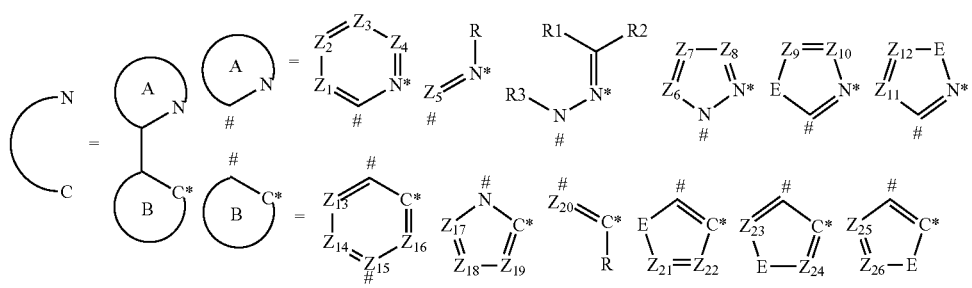

2) binds on the one hand via a sp²- and on the other hand via a carbene-carbon atom. The unit B can consist of a five or six ring, but can also be an open chain. The components Z13 to Z26 consist either of the fragments CR(X) (R(X)=organic moiety defined as R1-R20, see below) or N, E can be either NR, O or S. ("*" denotes the atom forming the complex bond, "#" denotes the atom that is bound to the second unit):

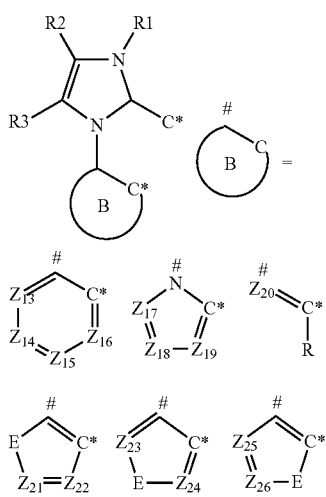

In the formulas given herein, R1 to R20 are organic groups that can be identical or different from each other. The organic groups can be in particular chosen from: hydrogen, halogen or groups, that are bound via oxygen (—OR), nitrogen (—NR$_2$) or silicon (—SiR$_3$), as well as alkyl-, aryl-, heteroaryl- and alkenyl groups or substituted alkyl-, aryl-, heteroaryl- and alkenyl groups with substituents like halogen, alkyl groups and further generally known donor and acceptor groups. The organic groups R1 to R20 can also lead to annulated ring systems. The groups are R1 to R20 comprise preferably 1 to 30 C atoms, particularly 1 to 20 C atoms. In order to ensure solubility, long chain (also branched), alkyl chains (C$_1$-C$_{30}$) and short chain polyether [e.g. polymers (—OCH$_2$CH$_2$O—)$_n$, n<500] are preferred. The alkyl chains can also be modified with polar groups e.g. with alcohols, aldehydes, amines, carbonic acids, ethers, phosphoric acid ethers, phosphonic acid, which allow for a further increase of solubility.

The rest R refers, as used herein, to organic groups (analogously to the definition to R1-R20). The organic groups can be in particular chosen from: hydrogen, halogen or groups, that are bound via oxygen (—OR), nitrogen (—NR$_2$) or silicon (—SiR$_3$), as well as alkyl-, aryl-, heteroaryl- and alkenyl groups or substituted alkyl-, aryl-, heteroaryl- and alkenyl groups with substituents like halogen, alkyl groups and further generally known donor and acceptor groups. The organic groups can also lead to annulated ring systems. In order to ensure solubility, long chain (also branched) alkyl chains (C1-C30) and short chain polyether [e.g. polymers (-OCH$_2$CH$_2$O—)$_n$, n<500]. The alkyl chains can also be modified with polar groups e.g. with alcohols, aldehydes, amines, carbonic acids, ethers, phosphoric acid ethers, phosphonic acids, which allow for a further increase of solubility.

The rest R', R" refer herein to organic groups (analogously to the definitions of R1 to R20), that can be identical or independent from each other. The organic groups can be in particular chosen from: hydrogen, halogen or groups, that are bound via oxygen (—OR), nitrogen (—NR$_2$) or silicon (—SiR$_3$), as well as alkyl-, aryl-, heteroaryl- and alkenyl groups or substituted alkyl-, aryl-, heteroaryl- and alkenyl groups with substituents like halogen, alkyl groups and further generally known donor and acceptor groups. The organic groups can also lead to annulated ring systems. In order to ensure solubility, long chain (also branched) alkyl chains (C1-C30) and short chain polyether [e.g. polymers (-OCH$_2$CH$_2$O—)$_n$, n<500]. The alkyl chains can also be modified with polar groups e.g. with alcohols, aldehydes, amines, carbonic acids, ethers, phosphoric acid ethers, phosphonic acids, which allow for a further increase of solubility.

R(X) refers herein to organic groups (analogously to the definitions of R1 to R20) that can be identical or independent from each other. X is a sequential number for numbering the moieties R (e.g. R1, R2, . . . ). The organic groups can be in particular chosen from: hydrogen, halogen or groups, that are bound via oxygen (—OR), nitrogen (—NR$_2$) or silicon (—SiR$_3$), as well as alkyl-, aryl-, heteroaryl- and alkenyl groups or substituted alkyl-, aryl-, heteroaryl- and alkenyl groups with substituents like halogen, alkyl groups and further generally known donor and acceptor groups. The organic groups can also lead to annulated ring systems. In order to ensure solubility, long chain (also branched) alkyl chains (C1-C30) and short chain polyether [e.g. polymers (—OCH$_2$CH$_2$O—)$_n$, n<500] are preferred. The alkyl chains can also be modified with polar groups e.g. with alcohols, aldehydes, amines, carbonic acids, ethers, phosphoric acid ethers, phosphonic acids, which allow for a further increase of solubility.

Alkyl moeities, as described herein, refer in particular to C1 to C30, preferably C1 to C20 alkyl moieties, particularly preferred to C1 to C10. Alkyl moeities can also form a ring.

Alkenyl and alkine moieties are preferably of 1 to 30, in particular of 2 to 20 C atoms, particularly preferred of 2 to 8.

Aryl groups are preferably systems with 5 to 30, in particular 5 to 10 ring atoms, wherein preferably 1 to 4 hetero-atoms, chosen from O, N, P or S are contained therein.

The ligand units A and/or B of the α-diimine ligands, carbene ligands and cyclo-metal forming ligands generally defined above can also form bridges with NL and/or AL

TABLE 1

Some examples of double complex salts, that are preferably used as absorbers in OSCs (OPVs). The absorption of materials go into the near infared range.
Compound

[Pt(CN-cyclododecyl)$_4$][Pt(CN)$_4$]
[Pt(phen)(CN-cyclohexyl)$_2$](Pt(CN)$_4$]
{[Pt(phen)(CN-cyclododecyl)Cl]$_2$[Pt(phen){CN-cyclododecyl)$_2$]$_2$[Pt(CN)$_4$]$_3$}
[Pt(p-CN—C$_6$H$_4$—CH$_3$)$_4$][Pt(CN)$_4$]
[Pt(p-CN—C$_6$H$_4$—C$_6$H$_{13}$)$_4$][Pt(CN)$_4$]
[Pt(p-CN—C$_6$H$_4$—C$_{10}$H$_{21}$)$_4$][Pt(CN)$_4$]
[Pt(p-CN—C$_6$H$_4$—C$_{12}$H$_{25}$)$_4$][Pt(CN)$_4$]
[Pt(p-CN—C$_6$H$_4$—C$_{14}$H$_{29}$)$_4$][Pt(CN)$_4$]
[Pt(CNR)$_4$][Pt(CN)$_4$]

CNR refers to common isonitrile ligands

In particular oligomers described in Table 1 are well suited for use in optoelectronic elements, in particular in OSCs. When manufacturing OSCs, all oligomers or columnar structures described herein can be used. Through the suitable choice of the oligomer, the desired absorption wavelength can be changed in a desired manner.

TABLE 2

Some concrete examples of double complex salts, double complex combinations, double complex doping that can preferably be used in optoelectronic components like lasers, diodes or transistors.

Compound

[Pd(bpy)$_2$][Pt(CN)]$_4$
[Pt(bpy)$_2$][Pd(CN)]$_4$
[Pd(bpy)$_2$][Pd(CN)]$_4$
[Pt(bpy)$_2$][Pt(CN)]$_4$
[Pd(4,4'-Dimethyl-2,2'-dipyridyl)$_2$][Pt(CN)]$_4$
[Pt(4,4'-Dimethyl-2,2'-dipyridyl)$_2$][Pd(CN)]$_4$
[Pd(4,4'-Dimethyl-2,2'-dipyridyl)$_2$][Pd(CN)]$_4$
[Pt(4,4'-Dimethyl-2,2'-dipyridyl)$_2$][Pt(CN)]4
[Pd(phen)$_2$][Pt(CN)$_4$]
[Pt(phen)$_2$][Pd(CN}$_4$]
[Pd(phen)$_2$][Pd(CN)$_4$]
[Pt(phen)$_2$][Pt(CN)$_4$]
{[Pd(bpy)$_2$][Pd(CN)$_4$]$_{1-x}$[Pt(CN)$_4$]$_x$} 0.00001 ≤ x ≤ 0.99999
{[Pd(bpy)$_2$][Pt(CN)$_4$]$_{1-x}$[Pd(CN)$_4$]$_x$} 0.00001 ≤ x ≤ 0.99999
{[Pt(bpy)$_2$][Pd(CN)$_4$]$_{1-x}$[Pt(CN)$_4$]$_x$} 0.00001 ≤ x ≤ 0.99999
{[Pt(bpy)$_2$][Pt(CN)$_4$]$_{1-x}$[Pd(CN)$_4$]$_x$} 0.00001 ≤ x ≤ 0.99999
{[Pd(CNR)$_4$][Pd(CN)$_4$]$_{1-x}$[Pt(CN)$_4$]$_x$} 0.00001 ≤ x ≤ 0.99999
{[Pd(CNR)$_4$][Pt(CN)$_4$]$_{1-x}$[Pd(CN)$_4$]$_x$} 0.00001 ≤ x ≤ 0.99999
{[Pt(CNR)$_4$][Pd(CN)$_4$]$_{1-x}$[Pt(CN)$_4$]$_x$} 0.00001 ≤ x ≤ 0.99999
{[Pt(CNR)$_4$][Pt(CN)$_4$]$_{1-x}$[Pd(CN)$_4$]$_x$} 0.00001 ≤ x ≤ 0.99999
[Pd(CNR)$_4$][Pt(CN)$_4$]
[Pt(CNR)$_4$][Pd(CN)$_4$]
[Pd(CNR)$_4$][Pd(CN)$_4$]
[Pt(bpy)(en)][Pd(CN)$_4$]
[Pd(bpy)(en)][Pt(CN)$_4$]
[Pd(bpy)(en)][Pd(CN)$_4$]
[Pt(bpy)(en)][Pt(CN)4]
[Pt(phen)(en)][Pd(CN)4]
[Pd(phen)(en)][Pt(CN)4]
[Pd(phen)(en)][Pd(CN)4]
[Pt(phen)(en)][Pt(CN)4]
[Pt(CNCH3)4][Pd(CN)4]
[Pd(CNCH3)4][Pt(CN)4]
[Pt(CNCH3)4][Pt(CN)4]
[Pd(CNCH3)4][Pd(CN)4]
[Pt(CNC2H5)4][Pd(CN)4]
[Pd(CNC2H5)4][Pt(CN)4]
[Pt(CNC2H5)4][Pt(CN)4]
[Pd(CNC2H5)4][Pd(CN)4]
[Pt(CN-t-C4H9)4][Pd(CN)4]
[Pd(CN-t-C4H9)4][Pt(CN)4]
[Pt(CN-t-C4H9)4][Pt(CN)4]
[Pd(CN-t-C4H9)4][Pd(CN)4]
[Pt(CN-cyclododecyl)4][Pd(CN)4]
[Pd(CN-cyclododecyl}4][Pt(CN)4]
[Pd(CN-cyclododecyl)4][Pd(CN)4]
[Pd(CN-cyclododecyl)$_4$][Pd(CN)4]
[Pt(phen)(CN-cyclohexyl)$_2$][Pd(CN)$_4$]
[Pd(phen)(CN-cyclohexyl)$_2$][Pt(CN)$_4$]
[Pd(phen)(CN-cycloheyl)$_2$][Pd(CN)$_4$]
[Pt(CN-n-tetradecyl)$_4$][Pd(CN)$_4$]
[Pd(CN-n-tetradecyl)$_4$][Pt(CN)$_4$]
[Pt(CN-n-tetradecyl)$_4$][Pt(CN)$_4$]
[Pd(CN-n-tetradecyl)$_4$][Pd(CN)$_4$]
{[Pt(phen)(CN-cyclododecyl)Cl]$_2$[Pt(phen)(CN-cyclododecyl)$_2$]$_2$[Pd(CN)$_4$]$_3$}
{[Pd(phen)(CN-cyclododecyl)Cl]$_2$[Pd{phen)(CN-cyclododecyl)$_2$]$_2$[Pt(CN)$_4$]$_3$}
{[Pt(phen)(CN-cyclododecyl)Cl]$_2$[Pd(phen)(CN-cyclododecyl)$_2$]$_2$[Pt(CN)$_4$]$_3$}
{[Pd(phen)(CN-cyclododecyl)Cl]$_2$[Pt(phen)(CN-cyclododecyl)$_2$]$_2$[Pt(CN)$_4$]$_3$}
{[Pt(phen)(CN-cyclododecyl)Cl]$_2$[Pd(phen)(CN-cyclododecyl)$_2$]$_2$[Pd(CN)$_4$]$_3$}
{[Pd(phen)(CN-cyclododecyl)Cl]$_2$[Pt(phen)(CN-cyclododecyl)$_2$]$_2$[Pd(CN)$_4$]$_3$}
{[Pd(phen)(CN-cyclododecyl)Cl]$_2$[Pd(phen)(CN-cyclododecyl)$_2$]$_2$[Pd(CN)$_4$]$_3$}
[Pt(p-CN—C$_6$H$_4$—C$_{10}$H$_{21}$)$_4$][Pd(CN)$_4$]
[Pd(p-CN—C$_6$H$_4$—C$_{10}$H$_{21}$)$_4$][Pt(CN)$_4$]
[Pd(p-CN—C$_6$H$_4$—C$_{10}$H$_{21}$)$_4$][Pd(CN)$_4$]
[Pt(p-CN—C$_6$H$_4$—CH$_3$)$_4$][Pd(CN)$_4$]
[Pd(p-CN—C$_6$H$_4$—CH$_3$)$_4$][Pt(CN)$_4$]
[Pd(p-CN—C$_6$H$_4$—CH$_3$)$_4$][Pd(CN)$_4$]
[Pt(p-CN—C$_6$H$_4$—C$_6$H$_{13}$)$_4$][Pd(CN)$_4$]
[Pd(p-CN—C$_6$H$_4$—C$_6$H$_{13}$)$_4$][Pt(CN)$_4$]
[Pd(p-CN—C$_6$H$_4$—C$_6$H$_{13}$)$_4$][Pd(CN)$_4$]
[Pt(p-CN—C$_6$H$_4$—C$_{12}$H$_{25}$)$_4$][Pd(CN)$_4$]
[Pd(p-CN—C$_6$H$_4$—C$_{12}$H$_{25}$)$_4$][Pt(CN)$_4$]
[Pd(p-CN—C$_6$H$_4$—C$_{12}$H$_{25}$)$_4$][Pd(CN)$_4$]
[Pt(p-CN—C$_6$H$_4$—C$_{14}$H$_{29}$)$_4$][Pd(CN)$_4$]
[Pd(p-CN—C$_6$H$_4$—C$_{14}$H$_{29}$)$_4$][Pt(CN)$_4$]
[Pd(p-CN—C$_6$H$_4$—C$_{14}$H$_{29}$)$_4$][Pd(CN)$_4$]

CNR refers to common isonitrile ligands.

Because of the opposed charges of the metal complexes used according to the invention, the electrostatic interaction (ionic bonding) leads to a pronounced stabilization of the M-M bond, which leads, among others, to poor solubility of such compounds. Although this simplifies the synthesis, since the double complex salts precipitate almost instantly when uniting the corresponding soluble components, at the same time, this complicates analytics as well as applications. Due to the low fugacity common for salts, a vacuum sublimation is not feasible and therefore, for producing thin layers, wet chemical procedures (e.g. spin coating, printing) need to be performed. This requires on the one hand a certain solubility of the compound. This is, however, not the case if the double complex salt can be used as a dispersion or if diffusion can be used to introduce the compound.

Platinum double complex salts of the general formula [L1L2L3L4Pt]$^{2+}$[Pt(AL1)$_4$]$^{2-}$ are generally insoluble. In this example, ligands L1 to L4 are neutral, L1 to L4 can also bound to each other, i.e. can form multidentate ligands. They thereby make up complexes, which e.g. comprise either a) one bi-dentate and two mono-dentate ligands, b) two bi-dentate ligands, c) one tri-dentate and one mono-dentate ligand or d) one quad-dentate ligand. For example, the neutral ligand can be α-diimine, like 2,2'-bipyridine or 1,10-phenanthroline, and AL1 can be one cyanide-, chloride-, bromide- or iodide-ion. Because of their excellent photo-physical properties, these double complex salts are good candidates for optoelectronic applications (OSCs).

Solubilization as a Production Technique

Surprisingly, double complex salts can be modified such that they solubilize either as oligomers or in polar solvents also as ions. The present invention thereby makes use of the fact that the bonds within the complex column are strong due to the M-M interactions, but that there is generally only weak van der Weals interactions between these columns. Through a substitution at the periphery of the ligands with a large organic moiety R, the M-M interactions are surprisingly not impeded, but the orientation of the different columns is disturbed such that they can no longer easily arrange themselves into a crystal lattice. The substitution can be formed both at the positively charged complexes as well as at the negatively charged components. A substitution at both is also possible. Thereby, the solubility is reached.

For all embodiments described herein, a solubilization of the double complex salt is particularly preferred. Therefore, at least one of the ligands comprises a large organic group for increasing the solubility, in particular one or several alkyl groups with 1 to 200 C atoms, preferably with 9 to 30 C atoms, and/or one or several polysiloxane groups (—OSiR$_2$)$_n$—OSiR'$_3$ with n=1 to 200, in particular n=5 to 30 and/or one or more polyether groups, in particular (-OCH$_2$—)$_n$—OR or (-OCH$_2$CH$_2$)$_n$—OR with n=1 to 200, in particular n=1 to 200, in particular n 2 to 30, wherein R is as defined herein and R' has the meaning given for R, preferably R and R' are C1 to C6 alkyl groups.

The examples given herein shall clarify the principles for the use of optoelectronic devices without limiting the general concept of the invention.

For simple OSCs, as shown in FIGS. 2 and 3, it is important to obtain high absorption over the range of the near UV, the visible range of the spectrum up to the red range or to the near infrared part of the spectrum. For these, preferably oligomers/columnar structures are used which have a comparably small M-M distances. For stacked OSCs, high absorption in the blue, or in the green, or in the red part of the spectrum of the spectrum of the sun light are particularly preferred. The absorption is determined through the suitable choice of the M-M distances.

Figure 4B:
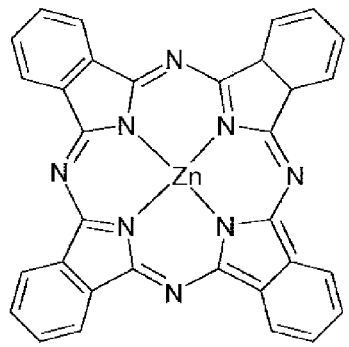
FIG. 4B shows examples of p-conductor materials for OSCs in accordance with an embodiment of the present invention.
Figure 4B:
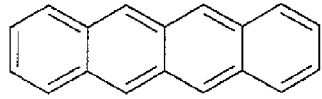
Figure 4B:
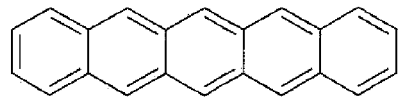
Figure 4B:
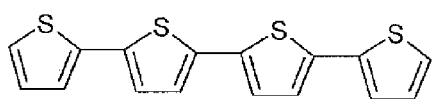
Figure 4B:
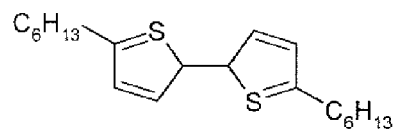
Figure 4B:
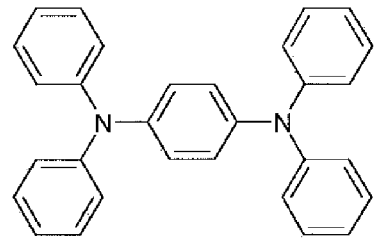
Figure 4B:
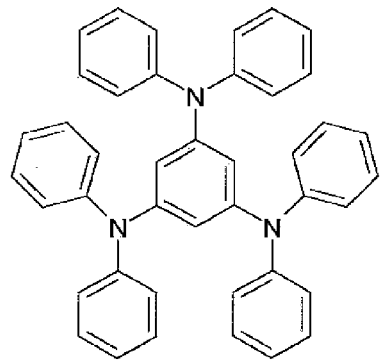
Figure 4B:
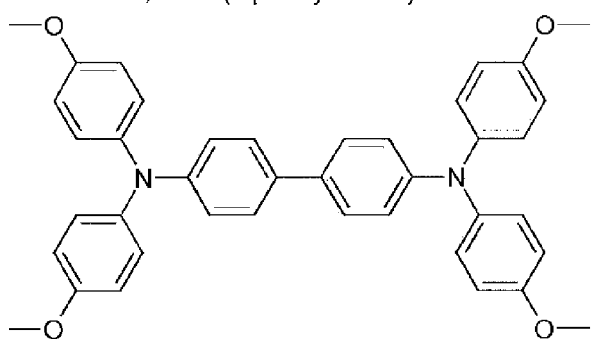

Principle remarks regarding the assembly of an OSC (FIG. 2)
1. As a carrier material, glass or any other suitable solid or flexible transparent material can be used.
2. ITO=indium-zinc oxide.
3. ETL=electron transport layer. For example a C$_{60}$ layer or an n-doped C$_{60}$ layer.
4. Light absorbing layer with the absorbing materials according to the invention. Preferably, the solubilizable oligomers/columnar structures described herein are present depending on the use in 5 wt % to 100 wt % (particularly preferred from 30 to 100%) and can, for example, be solubilized in organic solvents and applied (method A). In another preferred embodiment, the oligomers/columnar structures can (when the solubility is not sufficient) be applied as a dispersion (method B) in a suitable matrix material or as a 100% layer in a wet chemical fashion. In a further embodiment, method C can also be used as described. As matrix materials a suitable electron or hole conducting substance (or a mixture thereof) can be applied. Some examples for the n- and p-conductor materials are given in FIGS. 4A and 4B.
5. HTL=hole transport layer, MeO-TPD=N,N,N',N'-tetrakis-(4-methoxyphenyl)-benzidine. The HTL matrix material can also be doped with a p-dopend, e.g. MeO-TPD+F$_4$-TCNQ (tetrafluoro-tetracyano-chinodimethane).
6. The conducting metal layer is vapor deposited. Au represents an example. Other metals can also be used.

FIG. 3 shows an embodiment of the invention.

A further aspect of the invention is an optoelectronic apparatus, in particular a light absorbing apparatus comprising (i) an anode, (ii) a cathode and (iii) an absorption layer, arranged between and in direct or indirect contact with the anode or cathode, comprising at least one oligomer as defined herein.

The optoelectronic devices according to the invention are preferably manufactured chemically.

Example of a Synthesis of a Soluble Pt-Double Complex Salt (for Exemplifying the Synthesis):

[Pt(4,4'-Dinonyl-2,2'-dipyridyl)$_2$][Pt(CN)$_4$]

Using the example of a double complex salt [Pt(bpy)$_2$][Pt(CN)$_4$], the concept of solubilizing the metal-metal double complex salts shall be elucidated. Through use of bi-pyridines that are substituted in 4,4'-positions with each a CH$_3$(CH$_2$)$_8$-alkyl group, it is possible to solubilize the unsubstituted, unsoluble compound.

Synthesis of [Pt(4,4'-Dinonyl-2,2'-dipyridyl)$_2$][BF$_4$]$_2$

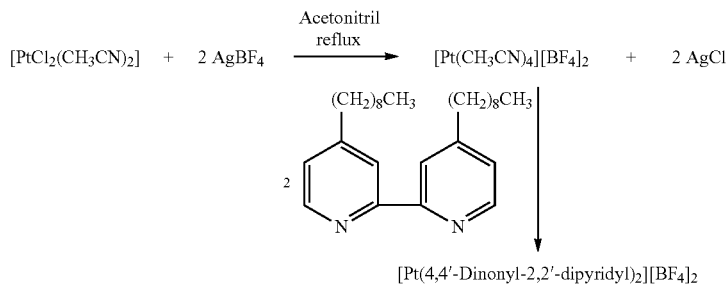

The synthesis is performed according to a modified synthesis found in literature (compare: A. Boixasse, J. Pons, X. Solans, M. Fontbardia, J. Ros, *Inorg. Chim. Acta* 2004, 357, 827.)

[PtCl$_2$(CH$_3$CN)$_2$] (0.300 g, 0.862 mmol) is suspended in 50 mL of dried acetonitril under N$_2$. AgBF$_4$ (0.336 g, 1.724 mmol) is added and the reaction mixture is refluxed for 20 h. Precipitated AgCl is removed by filtration and 4,4'-Dinonyl-2,2'-dipyridyl (0.705 g, 1.724 mmol) is added to a clear, colorless solution. Then, the solution remains under reflux for a further 20 h. The precipitated solid matter (remains of AgCl) is removed by filtration, and the clear, lightly yellow reaction solution is reduced using a rotary evaporator. The solution remains overnight in the freezer, which yields to a beige solid precipitating. The precipitate is suction cleaned and washed with ethanol and ether and subsequently dried. The solid is solubilized in dichloromethane and precipitated with ether. The fine, pale green precipitate is removed by filtration and dried in a desiccator.

Total formula: PtC$_{56}$H$_{88}$N$_4$B$_2$F$_8$ (1185.67 g/mol)
Elementary analysis: PtC$_{56}$H$_{88}$N$_4$B$_2$F$_8$ (1185.67 g/mol)
calculated: C, 56.68; H, 7.48; N, 4.72
measured: C, 56.68; H, 7.16; N, 4.56

Mass spectrometry: ES-MS, m/z=506.0 M$^{2+}$, 100%

Synthesis of [Pt(4,4'-dinonyl-2,2'-dipyridyl)$_2$][Pt(CN)$_4$]

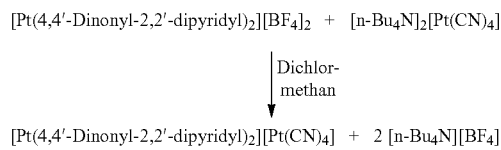

[Pt(4,4'-Dinonyl-2,2'-dipyridyl)$_2$][BF$_4$]$_2$ (0.0209 g, 0.0176 mmol) and [n-Bu$_4$N]$_2$[Pt(CN)$_4$] (0.0138 g, 0.0176 mmol) are separated and solubilized in 4 mL of dichloromethane. Subsequently, both solutions are combined. Overnight, the solvent is slowly evaporated yielding a yellow solid, which is washed with acetonitril (3 mL) and dried in a desiccator.

Total formula: Pt$_2$C$_{60}$H$_{88}$N$_8$·CH$_2$Cl$_2$ (1396.48 g/mol)

Elementary analysis: Pt$_2$C$_{60}$H$_{88}$N$_8$·CH$_2$Cl$_2$ (1396.48 g/mol)

calculated: C, 54.95; H, 6.76; N, 8.54 measured: C, 52.46; H, 6.50; N, 8.02

Figure 5:
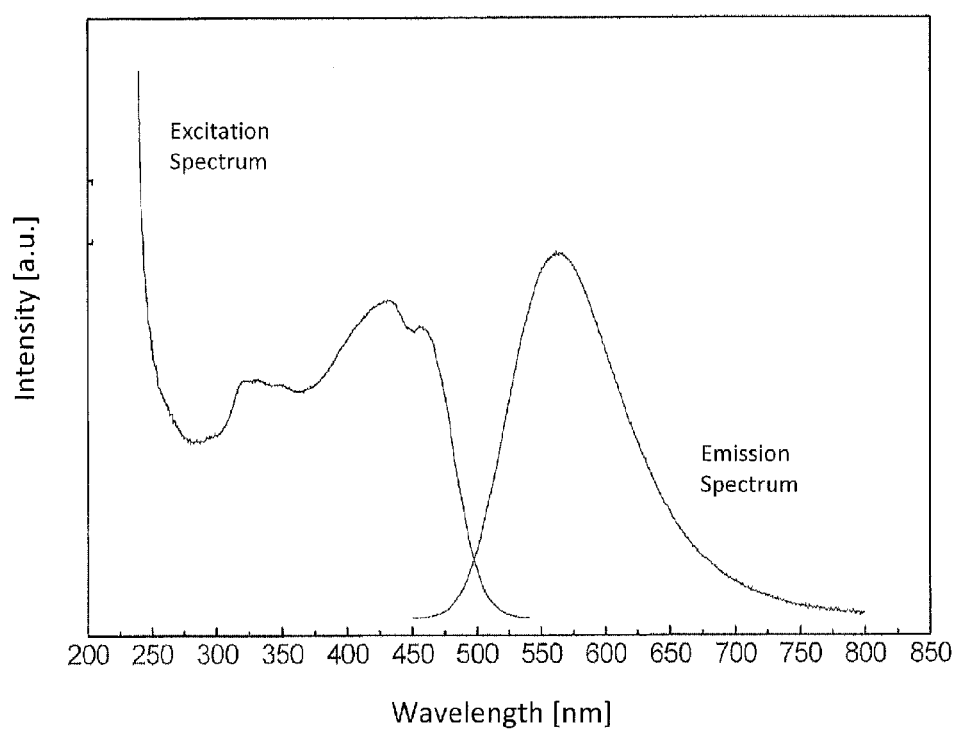
FIG. 5 shows an optical excitation spectrum and the emission spectrum of $[Pt(4,4'\text{-dinonyl-2,2'-dipyridyl})_2][Pt(CN)_4]$ in accordance with an embodiment of the present invention.

FIG. 5 shows the optical excitation spectrum and the emission spectrum of this novel substance.

Novelty and Advantages of the Present Invention for OSCs (OPVs) Through Use of Double Complex Salts Forming Columnar Structures.

As already mentioned, current technical problems arise when manufacturing efficient OSCs predominantly from the following two main reasons:

i) Lack of materials with high light absorption from the visible up to the near infared spectrum and ii) Lack of materials with high exciton diffusion lengths (long path of the excitation energy). This means that the materials shall have high exiton diffusion lengths in order to allow for an effective transfer to the boundary layer or to the dissociation area within the absorption layer, i.e. the exciton path must be fast and broad enough to enable an exciton dissociation.

The light absorption of a material for a given wavelength λ is described through the Lambert-Beer law:

$$-\log(I/I_0)=\epsilon(\lambda)cd$$

with I=intensity of the transmitted light, I$_0$=the intensity of the incoming/eradicated light, c=concentration of the absorbing substance and d=path length of the light in the material and $\epsilon(\lambda)$=molar decadal extinction coefficient. Under the assumption that 99% of the incoming light shall be absorbed, i.e. I/I$_0$=0.01 or $-\log$(I/I$_0$)=2 and disregarding reflections and a value of c=5 mol/l (typical solid concentration of metal complex/mixtures of the present invention) and d=100 nm (thickness of the light absorbing layer in an OSC), the necessary molar extinction coefficients can be estimated in the range of at least 10$^4$-10$^5$ mol$^{-1}$ cm$^{-1}$. Typically, the $\epsilon(\lambda)$ values of the most known materials in the visible or in the near IR spectrum are only 10$^3$-10$^4$ l mol$^{-1}$ cm$^{-1}$, rendering the extinction coefficients too low!

It was now surprisingly found that when using double complex salts that form oligomers or columnar structures in the optically active layers, the above given disadvantages do not occur. As already described above, quadratic-planar coordinated Pt(II) centers have a very strong tendency to show metal-metal interactions. The oligomers or columnar structures resulting therefrom have new electronic states (compared with the monomer units) and therefore exhibit also new absorption bands. The corresponding extinction coefficients are extremely high and lie within the $\epsilon(\lambda)$ region as required above. Columnar structures consisting of Pt(II) complexes can also be viewed as one-dimensional semi-conductors. Accordingly, such structures show very high exciton mobility.

It is to be emphasized that through the use of the metal complex salts described above a change of the absorption characteristics can be achieved. In particular, the M-M distances in the oligomers/columnar structures and the average chain lengths of these oligomers/columnar structures can be varied as desired. Therefore, the position of the absorption bands can be purposefully varied over a large range and one generate new oligomers/columnar structures whose absorption can be adapted to reach across the entire range of the spectrum (visible range of the spectrum up to the near infrared range). These high absorptions, e.g. up to the red or into the near infrared region, can be realized with small M-M distances in the oligomers/columnar structures of the double complex salts. Thereby, the absorbing material can be adapted optimally to the solar spectrum. Such oligomers/columnar structures are very well suited in particular for the use in the herein described OSCs and cannot be found in the state of the art. As examples herefore, oligomers/columnar structures of the double complex salts can be used that are made from monomers, which are described above.

Further important characteristic lies in the double complex salts chemical photo-chemical stability which makes them particularly suitable for use as absorbers in OSCs (OPVs).

Another important characteristic can be seen in the high-charge carrier mobility that the oligomers/columnar structures double complex salts that are to be used in optoelectronic devices according to the invention exhibit. Through the M-M interactions, the HOMO and LUMO are being delocalized over several molecules (building blocks oligomers/columnar structures). This leads to a marked improvement of the hole and electron mobility. As a result, the absorbing layer does not require additional components for improving the mobility, i.e. any limiting requirements regarding the matrix for a for good charge-carrier mobility can be disregarded when using these double complex salts in many applications. Thereby, it is possible to obtain a large improvement of efficiency and cheap assembly of OSCs (OPVs).

Handling of Double Complex Salts in OSCs

The handling/use of double complex salts in the optically relevant layers, i.e. the absorbing layer in the OSC is not obvious (simple), because the double complex salts are hardly or not at all soluble. Surprisingly, it is now possible to handle the materials in optoelectronic elements in various ways:

A Solubilizing

Through a solubilization of the components, the salts become well soluble but retain their advantageous optical properties. This is achieved by choosing at least for one of the organic groups at the ligands a particular embodiment. Specifically, in order to ensure solubility, preferably long chain—also branched—alkyl chains C1 to C30 and short chain polyether [e.g., polymers (—OCH2CH2O—)n, n<500] can be used. The alkyl chains can be also be modified with polar groups, e.g. with alcohols, aldehydes, amines, carboxylic acids, ethers, phosphoric acid ethers, phosphonic acids, that allow for further improvement of solubility.

B Dispersion

For the use of the oligomers/columnar structures of the invention that are little or not at all soluble, the application in the form of dispersions can be performed. Specifically, colloidal dispersions of the oligomers/columnar structures mixed or submerged in a suitable polymer can be applied. The concentration of the oligomers in the polymer is 2 to 10 wt-% or 10 to 90 wt.-%. It is, however, possible to apply the pure oligomer/columnar structure (i.e. without polymer) as a dispersion, thereby realizing 100% absorbing or emitter layers. If necessary, the oligomer strands/columnar structures can be decreased in size before introducing them into the polymer using ultrasound in the liquid phase. This is done through introducing the first component and adding the second, third, . . . component in the ultrasonic bath. The double complex salts are introduced into the polymer after filtration through micro/nano filters. This is also true for the application as a 100% emitter layer.

C Diffusion Methods

The use according to the invention of oligomers/columnar structures that are not or hardly soluble, the diffusion method is suitable, which is described for the first time herein, for manufacturing emission layers. Firstly, one of the in general soluble components of the double complex salts is introduced into the optically relevant polymer layer. The second component is then introduced onto this layer. By diffusion through the polymer layer, the second component moves towards the first component and forms the insoluble oligomer. Through washing of the second complex salt component, the procedure is stopped and desired double complex salt concentration has been reached.

When disposing the oligomers/columnar structures in one of the fashions described above during the manufacture of the OSCs, the oligomer strands are present in the absorbing layer in an unordered manner. When light falls upon this layer, part of it will be absorbed by an oligomer strand whereas another part will be reflected therefrom and will interact with neighboring strands. Again, a part of the light will be absorbed and reflected there. Until the incoming light has gone through the absorbing layer, this process of absorption and reflection will occur many times, which will improve the absorption efficiency compared with standard OSCs. In many OSCs according to the state of the art, the incoming light is already reflected at the surface of the absorbing layer and therefore cannot be used further.

D Orientation of the Complex Strands

Figure 6A:
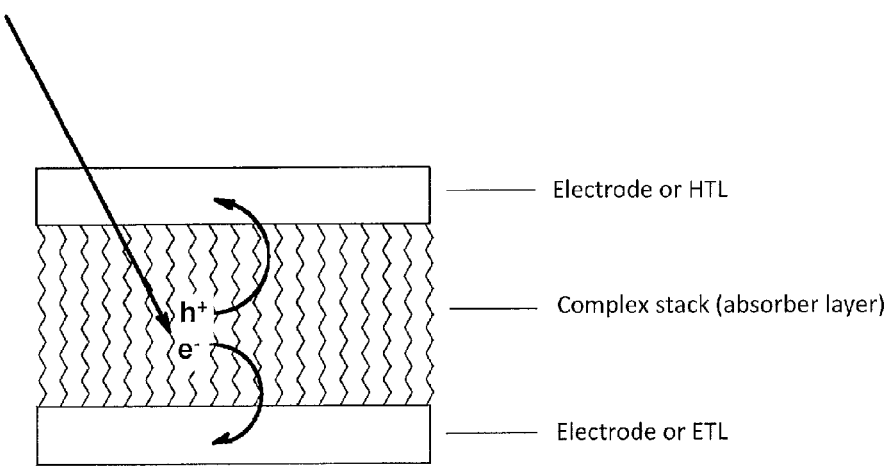
FIG. 6A shows a diagram of a component with columnar structures perpendicular to a substrate surface in accordance with an embodiment of the present invention.

As quasi one-dimensional structures, the electronic characteristics of the complex salts of the oligomers described herein are anisotropic. When randomly introducing the columnar structuring into a matrix or onto a substrate, isotropic characteristics of the optoelectronic component will result parallel to the surface. In an embodiment of the invention, the anisotropic character of the substance is used to realize device nano-architectures with special characteristics. This is illustrated in the following examples:

a) Columnar structures perpendicular to the substrate surface:
When the conditions are chosen such that the columnar structures grow perpendicular on a substrate surface (e.g. a (polymer) conductor or semi-conductor), an absorbing layer results that is characterized in addition to an increase in absorption by also the high charge-carrier mobility in a defined direction. The increase in absorption is achieved compared to the random orientation of the columnar structures in that these layers can be oriented optimally to the incoming direction of the light (see FIG. 6A, that shows a diagram of a component with columnar structures or oriented perpendicular to the surface of the substrate (HTL: hole transport layer), ETL: electron transport layer)).

b) Columnar structures parallel to a preferred direction:
Such structures can easily be manufactured from a dispersion of already formed columnar structures (see section A or B above) by applying the dispersion onto the preferred substrate and orienting the complex strands through shearing (e.g., using a brush or spatula) uniformly.

Figure 6B:
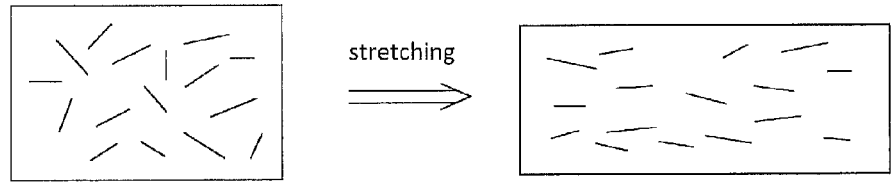
FIG. 6B shows a diagram of a component with columnar structures parallel to a preferred direction in accordance with an embodiment of the present invention.
Figure 6C:
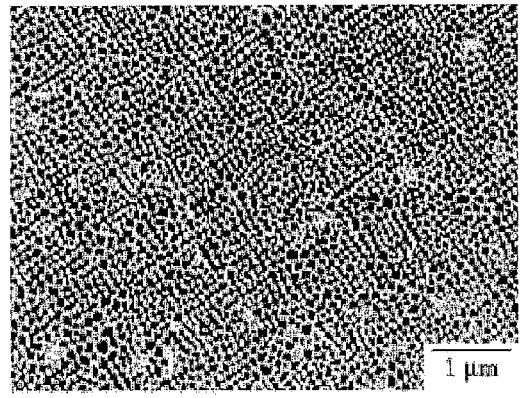
FIG. 6C shows a diagram of a component having nano-structured surfaces in accordance with an embodiment of the present invention.
Figure 6C:
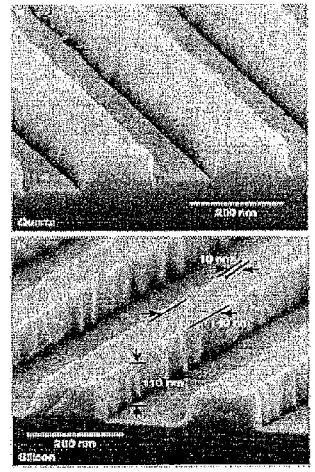

If the columnar structures are introduced into a matrix, the complex strands can be oriented through stretching of the film in the direction of the stretch (schematically shown in FIG. 6B).

c) Use of nano-structured surfaces:
A further possibility for orienting the columnar structures (perpendicular or parallel to the substrate surface) is the use of nano-structured surfaces. As known to the person of skill in the art, a number of metal oxides can be structured in the nano-range through electrochemical etching, through gas-phase evaporation or lithographical methods. In these nano-structures, the columnar structures can either grow directly or ready-built complex strands can be introduced. An example of a nano-structure built perpendicular on a substrate surface is the surface of $TiO_2$ (a semi-conductor), whose surface is structured in the form of honeycombs. In nano-structures that were generated, for example, through lithographic procedures, columnar structures can grow parallel or can be introduced as existing columnar strands. Such structures are shown in FIG. 6C (source of the figures: http://apchem.gifu-u.ac.jp/~pcl/minourahp/research/research_e.htm and http://140.116.176.21/www/english/R%20&%20D/research_projects.html).

d) Columnar structures as scaffolds for organic substances:
Columnar structures can additionally serve as a scaffold for polymer (matrix-) materials. Through the presence of the complex strands introduced in a polymer, the surrounding polymers can be prompted to partially crystallize (analogously to corresponding additives for polyolefines). Due to the presence of crystalline, polymer domains, the efficiency of, for example, charge-carrying materials can be increased, because the order and therefore also the conjugational length of the polymers increases.

Using the methods according to the above described sections a) to c), architectures are built that have strong anisotropic characteristics, which are advantageous for special OSC, sensor, transistor, or laser applications.

The invention claimed is:

1. A method for forming an organic solar cell (OSC) comprising:
providing an absorbing layer; and
incorporating an oligomer into the absorbing layer,
wherein the oligomer comprising
at least one positively charged metal complex
and at least one negatively charged metal complex,
wherein the metal complexes are of $$K_1=[L1L2L3L4M1]^{n+} \qquad \text{formula (I)}$$

and $$K2=[L5L6L7L8M2]^{n-} \qquad \text{formula (II)}$$

wherein M1 and M2 each is a metal center, chosen independently from each other from Ir(I), Rh(I), Pt(II), Pd(II) and Au(III) and
L1-L4 and L5-L8 each represent a neutral or charged ligand, wherein
n is 1 or 2.

2. The method of claim 1, wherein the oligomer is introduced into the absorbing layer in the form of a dispersion.

3. The method of claim 1, wherein the components of formula (1) are introduced into the absorbing layer as a solution and the components of formula (2) are introduced into the absorbing layer through diffusion.

4. The method of claim 1, wherein the oligomer is arranged perpendicularly to an electrode surface of the organic solar cell (OSC).

5. The method of claim 1, wherein the oligomer is arranged perpendicularly between two electrode surfaces of the organic solar cell (OSC) in a sandwich assembly.

6. The method claim 5, wherein the oligomer is oriented parallel to a substrate surface of the organic solar cell (OSC) and wherein the parallel orientation is achieved by one of alignment of dispersions of already-formed oligomers and or stretching of oligomers introduced into one of a polymer and double complex salt strands.

7. The method of claim 1, wherein the oligomer is introduced through an electrode surface of the organic solar cell (OSC) that was structured at a nano-scale through one of electrochemical etching, through chemical vapor deposition or lithographic methods, and wherein the oligomer is oriented depending on the nano-structuring either perpendicularly, parallel or in an unordered fashion to the electrode surface of the organic solar cell (OSC).

8. The method according to claim 1, wherein the oligomer comprises two to five positively charged complexes and two to five negatively charged complexes.

9. The method according to claim 1, wherein the oligomer is a double complex salt, wherein K1=[L1L2L3L4Pt(II)]⁺      (formula (1))

and

K2=[L5L6L7L8Pt(II)]      (formula (II)), wherein K1 is in particular one of the following formulas 1 or 2:

1

General formula of α-diimine complexes

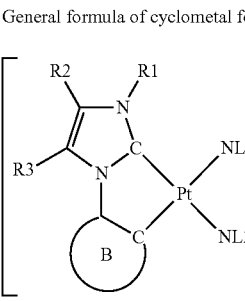

2

General formula of cyclometal forming carbene-Pt complexes

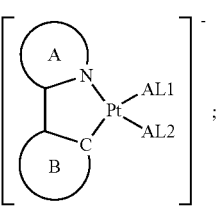

and
K2 is the following formula 24

24

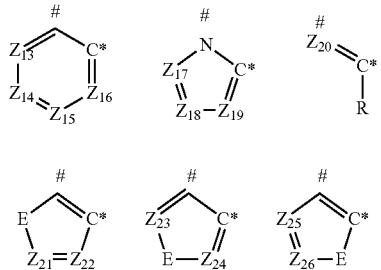

;

wherein R1 to R20 are each independently selected from the group consisting of hydrogen, halogen, —OR, —NR$_2$, —SiR$_3$, wherein R is a C$_1$ to C$_{30}$ carbohydrate moiety selected from the group consisting of a C$_6$ to C$_{20}$ carbohydrate moiety, alkyl, alkenyl, aryl or hetero-aryl with 1 to 5 heteroatoms chosen from O, NS wherein the alkyl, alkynyl, aryl or heteroaryl groups can be substituted with substituents selected from the group consisting of halogen, C$_1$ bis C$_{30}$ alkyl groups and/or NL1, NL2, NL3, NL4, each independently selected from the group consisting of carbonyl, nitryl, isonitryl or oxazole and AL1, AL2, AL3, AL4 are each selected from the group consisting of cyanide, chloride, bromide, iodide, RS⁻, RO⁻, SCN⁻, OCN⁻, aryl, alkenyl, alkynyl, or borate;

and wherein

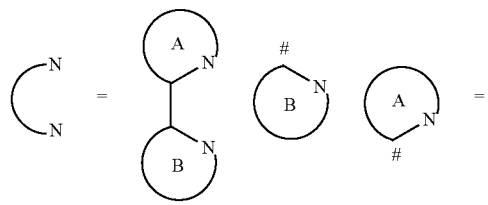

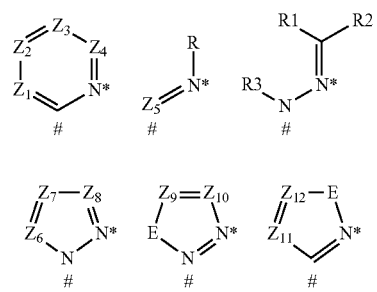

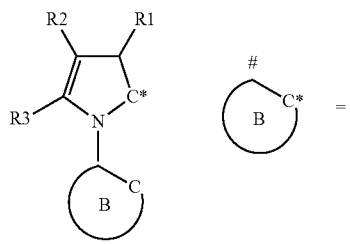

and

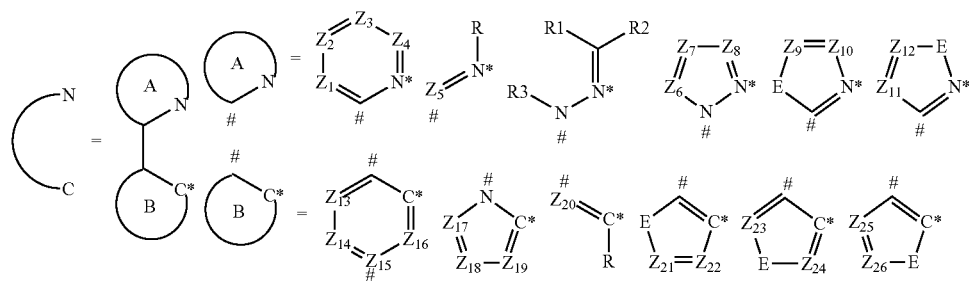

wherein the components Z1 to Z26 consisting of either the fragment CR(X) (R(X)=organic moiety defined as R1-R20) or N and E can be either NR, O or S.

10. The method according to claim 1, wherein the oligomer is a double complex salt, with $$K1=[L1L2L3L4Pd(II)]^+$$

and $$K_2=[L5L6L7L8Pd(II)]^-,$$

wherein $K_1$ is one of the following formulas 36 or 37:

General formula of α-diimine complexes

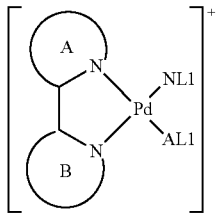

36

General formula of cyclometal forming carbene-Pd complexes

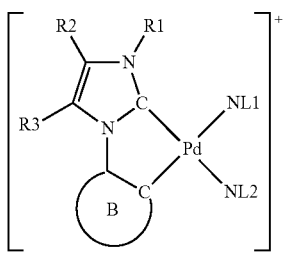

37 and
$K_2$ is from the following formula 41:
General formula:

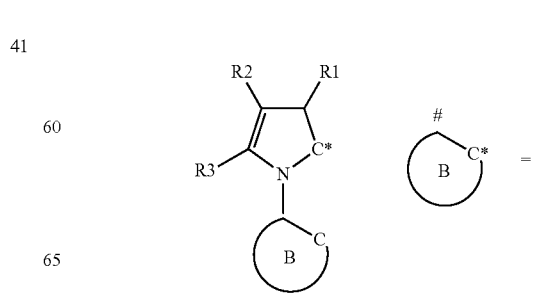

41 wherein R1 to R20 are each independently selected from the group consisting of hydrogen, halogen, —OR, —NR$_2$, —SiR$_3$, wherein R is a $C_1$ to $C_{30}$ carbohydrate moiety, alkyl, alkenyl, aryl or hetero-aryl with 1 to 5 hetero-atoms having O, NS wherein the alkyl, alkynyl, aryl or heteroaryl groups can be substituted with substituents selected from the group consisting of halogen, $C_1$ bis $C_{30}$ alkyl groups and/or NL1, NL2, NL3, NL4, each are independently selected from the group consisting of carbonyl, nitryl, isonitryl or oxazole and AL1, AL2, AL3, AL4 are each selected from the group consisting of cyanide, chloride, bromide, iodide, RS⁻, RO⁻, SCN⁻, OCN⁻, aryl, alkenyl, alkynyl, or borate, and wherein

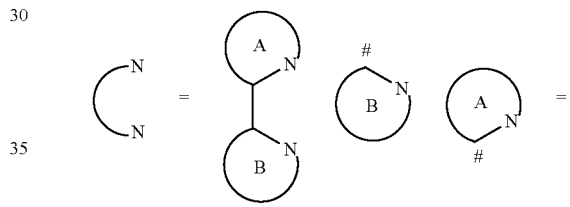

and

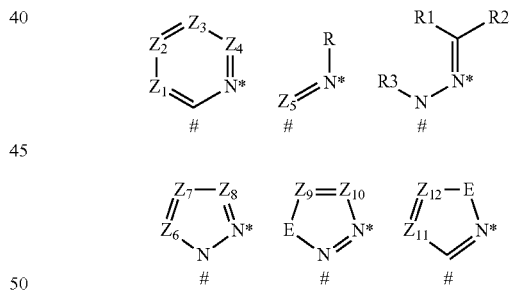

-continued

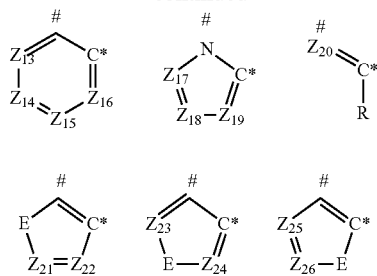

and

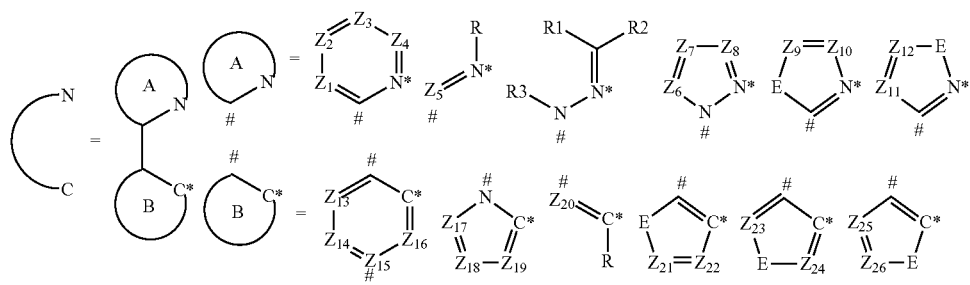

wherein the components Z1 to Z26 consisting of either the fragment CR(X) (R(X)=organic moiety defined as R1-R20) or N and E can be either NR, O or S.

11. The method of claim 1, wherein the oligomer is a double complex salt with $K_1 = [L1L2L3L4Ir(I)]^+$ and $K_2 = [L5L6L7L8Ir(I)]^-$, wherein $K_1$ is chosen from one of the general formulas 44 or 45:

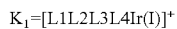

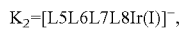

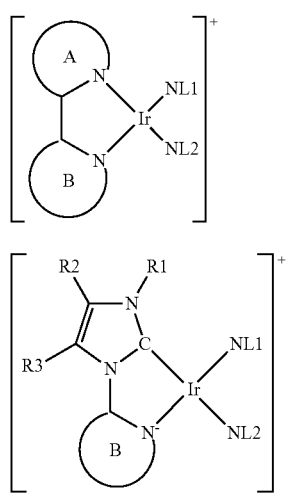

wherein R1 to R20 are each independently selected from the group consisting of hydrogen, halogen, —OR, —NR₂, —SiR₃, wherein R is a $C_1$ to $C_{30}$ carbohydrate moiety, alkyl, alkenyl, aryl or hetero-aryl with 1 to 5 hetero-atoms, having O, NS wherein the alkyl, alkynyl, aryl or heteroaryl groups can be substituted with substituents selected from the group consisting of halogen, $C_1$ bis $C_{30}$ alkyl groups and/or NL1, NL2, NL3, NL4, are each independently selected from the group consisting of carbonyl, nitryl, isonitryl or oxazole and AL1, AL2, AL3, AL4 are each individually selected from the group consisting of cyanide, chloride, bromide, iodide, RS⁻, RO⁻, SCN⁻, OCN⁻, aryl, alkenyl, alkynyl, or borate;

and wherein

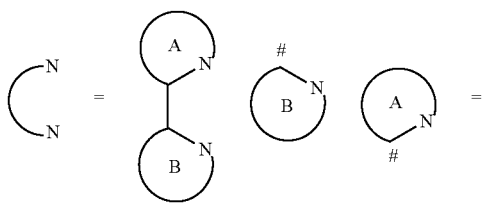

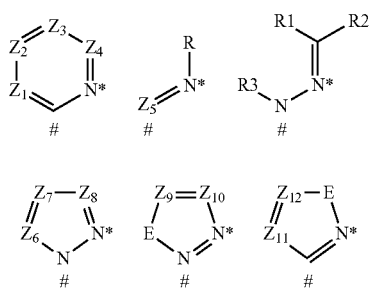

wherein the components Z1 to Z26 consisting of either the fragment CR(X) (R(X)=organic moiety defined as R1-R20) or N and E can be either NR, O or S.

12. The method according to claim 1, wherein the oligomer is a double complex salt with $K1 = [L1L2L3L4Rh(I)]^+$ and $K_2 = [L5L6L7L8Rh(I)]^-$, wherein $K_1$ is selected from one of formula 59 or 60

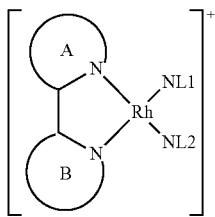

59

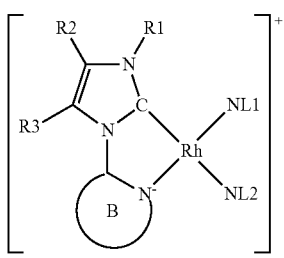

60 and
wherein $R_1$ to $R_{20}$ are each independently selected from the group consisting of hydrogen, halogen, —OR, —NR$_2$, —SiR$_3$, wherein R is a $C_1$ to $C_{30}$ carbohydrate moiety, alkyl, alkenyl, aryl or hetero-aryl with 1 to 5 hetero-atoms selected from O, NS wherein the alkyl, alkynyl, aryl or heteroaryl groups can be substituted with substituents selected from the group consisting of halogen, $C_1$ bis $C_{30}$ alkyl groups and/or NL1, NL2, NL3, NL4, are each independently selected from the group consisting of carbonyl, nitryl, isonitryl or oxazole and AL1, AL2, AL3, AL4 are each individually selected from the group consisting of cyanide, chloride, bromide, iodide, RS$^-$, RO$^-$, SCN$^-$, OCN$^-$, aryl, alkenyl, alkynyl, or borate;

and wherein

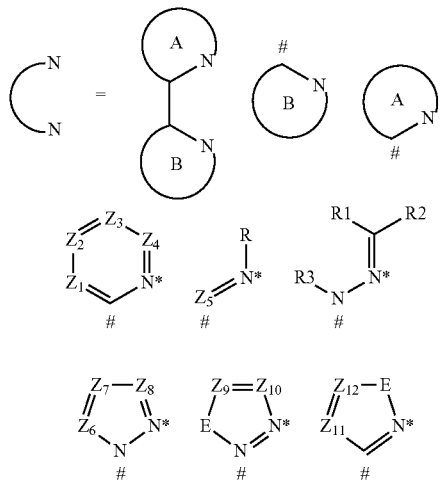

wherein the components Z1 to Z26 consisting of either the fragment CR(X) (R(X)=organic moiety defined as R1-R20) or N and E can be either NR, O or S.

13. The method according to claim 1, wherein the oligomer is a double complex salt, wherein $K1=[L1L2L3L4Pt(II)]2+$ and $K2=[L5L6L7L8Pt(II)]2$, wherein K1 is one of the following formulas 72, 73, 81 or 82:
general formulas:

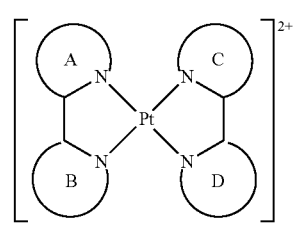

72

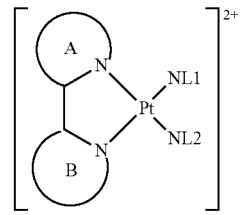

73

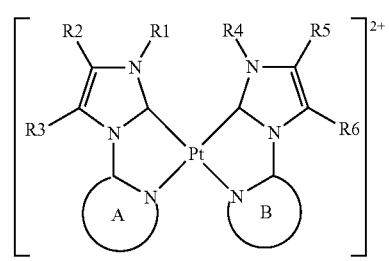

81

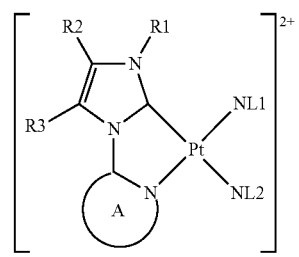

82 and wherein R1 to R20 are each independently selected from the group consisting of hydrogen, halogen, —OR, —NR$_2$, —SiR$_3$, wherein R is a $C_1$ to $C_{30}$ carbohydrate moiety, alkyl, alkenyl, aryl or hetero-aryl with 1 to 5 hetero-atoms, selected from O, NS, wherein the alkyl, alkynyl, aryl or heteroaryl groups can be substituted with substituents selected from the group consisting of halogen, $C_1$ bis $C_{30}$ alkyl groups and/or NL1, NL2, NL3, NL4, are each independently selected from the group consisting of carbonyl, nitryl, isonitryl or oxazole and AL1, AL2, AL3, AL4 are each individually selected from the group consisting of cyanide, chloride, bromide, iodide, RS$^-$, RO$^-$, SCN$^-$, OCN$^-$, aryl, alkenyl, alkynyl, or borate;

and wherein

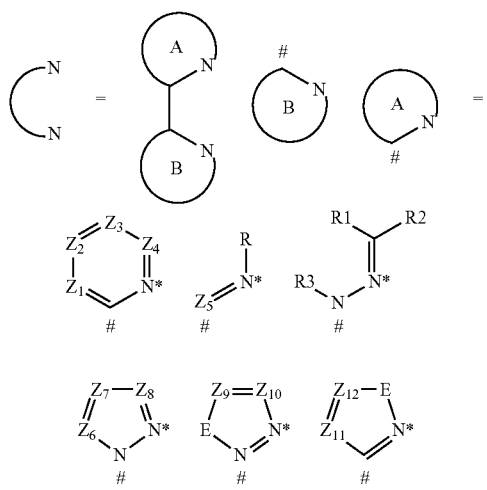

wherein the components Z1 to Z26 consisting of either the fragment CR(X) (R(X)=organic moiety defined as R1-R20) or N and E can be either NR, O or S;
and wherein rings C and D are defined analogously to A and B.

14. The method according to claim 1, wherein at least one of the ligands contains at least one of following: one or more alkyl groups C1-C200, one or more polysiloxane groups and the formula (—OSiR2-)nOSiR'3 with n=1-200, and one or more polyether groups, (—OCH2-)nOR or (—OCH2CH2)nOR with n=1-200 wherein an R and R' are each an alkyl group C1-C6.

15. The method of claim 1, wherein at least one of two or more of L1-L4 are connected to each other and two or more of L5-L8 are connected to each other.

16. A method for forming an organic solar cell (OSC) comprising:
providing an absorbing layer; and
incorporating a metal complex salt into the absorbing layer, wherein the metal complex salt comprises at least one positively charged metal complex and at least one negatively charge complex, wherein the metal complexes are of
at least one positively charged metal complex
and at least one negatively charged metal complex,
wherein the metal complexes are of $$K_1 = [L1L2L3L4M1]^{n+} \quad \text{formula (I)}$$

and $$K_2 = [L5L6L7L8M2]^{n-} \quad \text{formula (II)}$$

wherein M1 and M2 is each a metal center, chosen independently from each other from Ir(I), Rh(I), Pt(II), Pd(II) and Au(III) and
L1-L4 and L5-L8 each represent a neutral or charged ligand, wherein
n is 1 or 2.

17. The method of claim 16, wherein the metal complex salt is introduced into the absorbing layer using one a dispersion or wherein the components of formula (1) are introduced into the absorbing layer as a solution and the components of formula (2) are introduced into the absorbing layer through diffusion.

18. The method of claim 16, wherein at least one of two or more of L1-L4 are connected to each other and two or more of L5-L8 are connected to each other.

* * * * *

UNITED STATES PATENT AND TRADEMARK OFFICE
CERTIFICATE OF CORRECTION

PATENT NO. : 8,728,567 B2  
APPLICATION NO. : 13/125949  
DATED : May 20, 2014  
INVENTOR(S) : Yersin et al.

Page 1 of 1

It is certified that error appears in the above-identified patent and that said Letters Patent is hereby corrected as shown below:

In the specification:

Col. 2, line 58, please delete "are"

Col. 4, line 31, please delete "Is not be equal to" and replace with "can be not equal to"

Col. 31, line 65, please delete "für"

Col. 33, line 14, before "quadratic-planar, singly negatively charged Pd-complex" please insert --K1:--

Col. 34, line 64, after "L1 to L8 and" please insert --L1'--

Col. 37, line 40, please delete "are"

In the claims:

Claim 9, column 48, line 51, please change "C" to --C*--

Claim 10, column 50, line 64, please change "C" to --C*--

Signed and Sealed this  
Fifth Day of August, 2014

Michelle K. Lee  
*Deputy Director of the United States Patent and Trademark Office*